(12) United States Patent
Zhang et al.

(10) Patent No.: US 12,388,114 B2
(45) Date of Patent: Aug. 12, 2025

(54) IN SITU GENERATED SOLID ELECTROLYTE FOR ENERGY STORAGE

(71) Applicants: UCHICAGO ARGONNE, LLC, Chicago, IL (US); MERCEDES-BENZ RESEARCH & DEVELOPMENT NORTH AMERICA, INC., Sunnyvale, CA (US)

(72) Inventors: Zhengcheng Zhang, Naperville, IL (US); Quinton James Meisner, Westmont, IL (US); Tobias Glossmann, Birmingham, MI (US)

(73) Assignees: UCHICAGO ARGONNE, LLC, Chicago, IL (US); MERCEDES-BENZ RESEARCH & DEVELOPMENT NORTH AMERICA, INC., Sunnyvale, CA (US)

( * ) Notice: Subject to any disclaimer, the term of this patent is extended or adjusted under 35 U.S.C. 154(b) by 694 days.

(21) Appl. No.: 17/705,530

(22) Filed: Mar. 28, 2022

(65) Prior Publication Data

US 2023/0327197 A1    Oct. 12, 2023

(51) Int. Cl.
*H01M 10/0567* (2010.01)
*C07D 331/02* (2006.01)
(Continued)

(52) U.S. Cl.
CPC ...... *H01M 10/0567* (2013.01); *C07D 331/02* (2013.01); *H01M 4/382* (2013.01);
(Continued)

(58) Field of Classification Search
CPC ............ H01M 10/0567; H01M 4/382; H01M 10/052; H01M 10/0565; H01M 2300/0025; H01M 2300/0082; H01M 2300/0085; H01M 2300/0091; C07D 331/02; Y02E 60/10
See application file for complete search history.

(56) References Cited

U.S. PATENT DOCUMENTS

| 10,700,357 B2 * | 6/2020 | Zhamu | H01M 4/133 |
| 2003/0003370 A1 * | 1/2003 | Arai | H01M 10/052 |
| | | | 429/343 |

(Continued)

FOREIGN PATENT DOCUMENTS

| CN | 1880349 | 12/2006 |
| CN | 110911739 | 3/2020 |

(Continued)

OTHER PUBLICATIONS

Zhao, Q., Stalin, S., Zhao, CZ. et al. Designing solid-state electrolytes for safe, energy-dense batteries. Nat Rev Mater 5, 229-252 (2020). (Year: 2020).*

(Continued)

*Primary Examiner* — Basia A Ridley
*Assistant Examiner* — Sarah A Applegate
(74) *Attorney, Agent, or Firm* — Foley & Lardner LLP

(57) ABSTRACT

A battery includes a cathode including a cathode active material, an anode comprising lithium, and an electrolyte including an aprotic solvent, a lithium salt, and a compound or mixture of two or more different compounds each containing at least one epi-sulfide group.

12 Claims, 8 Drawing Sheets

(51) Int. Cl.
*H01M 4/38* (2006.01)
*H01M 10/052* (2010.01)
*H01M 10/0565* (2010.01)

(52) U.S. Cl.
CPC ..... *H01M 10/052* (2013.01); *H01M 10/0565* (2013.01); *H01M 2300/0025* (2013.01); *H01M 2300/0082* (2013.01); *H01M 2300/0085* (2013.01); *H01M 2300/0091* (2013.01)

(56) References Cited

U.S. PATENT DOCUMENTS

2013/0189589 A1 7/2013 Hashaikeh et al.
2021/0075019 A1* 3/2021 Okubo ................... H01M 4/13

FOREIGN PATENT DOCUMENTS

| CN | 110994016 | 4/2020 |
| CN | 111540947 | 8/2020 |
| CN | 111816925 | 10/2020 |
| CN | 111864259 | 10/2020 |
| CN | 111883824 | 11/2020 |
| CN | 112259789 | 1/2021 |
| JP | 1972051948 | * 11/1971 |

OTHER PUBLICATIONS

Translated JP1972051948 (Year: 1972).*
Archer, et al., "Designing solid-state electrolytes for safe, energy-dense batteries," National Review Materials, 5,(2020), pp. 229-252.
Archer, et al., "Solid-state polymer electrolytes with in-built fast interfacial transport for secondary lithium batteries," Nature Energy 4, (2019), pp. 365-373.
Guo, et al., "Progress of the interface design in all-solid-state Li—S batteries", Advanced Functional Materials, 1707533 (2018), pp. 1-16.
Zhong, et al., "A novel quasi-solid state electrolyte with highly effective polysulfide diffusion inhibitioin for lithium-sulfur batteries," Scientific Reports 6, 25484 (2016), pp. 1-7.
Zhou, et al., "High-safety all-solid-state lithium-metal battery with high-ionic-conductivity thermoresponsive solid polymer electrolyte," Nano Letters, 19, (2019), pp. 3066-3073.

* cited by examiner

IN SITU GENERATED SOLID ELECTROLYTE FOR ENERGY STORAGE

GOVERNMENT RIGHTS

This invention was made with government support under Contract No. DE-AC02-06CH11357 awarded by the United States Department of Energy to UChicago Argonne, LLC, operator of Argonne National Laboratory. The government has certain rights in the invention.

FIELD

The present technology is generally related to lithium ion batteries. More specifically, it is related to the use of polymerizeable sulfur compounds having an epi-sulfide functionality to prepare solid-state and/or gelled electrolytes.

SUMMARY

In one aspect, a compound of Formula I is provided:

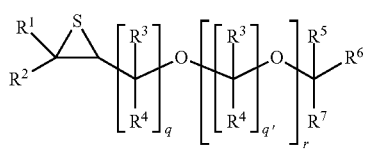

(I)

where each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl; q is 0, 1, 2, or 3; q' is 1, 2, 3, or 4; and r is at least 1. Illustrative compounds of Formula I include $G_1S$ or $SG_xS$:

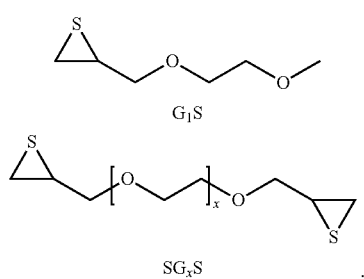

In another aspect, an electrolyte for a Li—S battery includes an aprotic solvent, a lithium salt, and a compound of Formula I, as described above. In some embodiments, the compound of Formula I, is represented as a mixture of compounds of Formula IA and Formula IB:

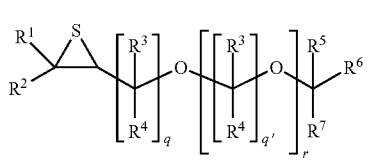

(IA)

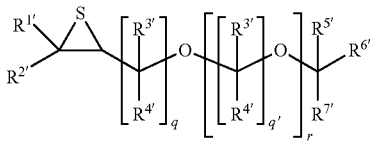

(IB)

wherein each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl; each $R^{1'}$, $R^{2'}$, $R^{3'}$, $R^{4'}$, $R^{5'}$, $R^{6'}$, and $R^{7'}$ is individually H, alkyl, alkoxy, aryl, aralkyl, heteroaryl, heteroaralkyl, heterocyclylalkoxyl, heterocyclyl, or heterocyclylalkyl, with the proviso that at least one $R^{1'}$, $R^{2'}$, $R^{3'}$, $R^{4'}$, $R^{5'}$, $R^{6'}$, and $R^{7'}$ contains a heterocyclyl group; each q is individually 0, 1, 2, or 3; each q' is individually 1, 2, 3, or 4; and each r individually is at least 1.

In further aspect, a battery includes a cathode comprising a cathode active material, an anode comprising lithium, and an electrolyte comprising an aprotic solvent, a lithium salt, and a compound or mixture of two or more different compounds each containing at least one epi-sulfide group. The electrolytes may include any of those as described herein. The at least one epi-sulfide group may include any of the compounds having thio-epoxy group as described herein.

In yet a further aspect, a process of forming a gelled electrolyte includes providing a battery or battery housing including a cathode having a cathode active material, an anode including lithium, and an electrolyte that includes an aprotic solvent, a lithium salt, and a compound or mixture of two or more different compounds each containing at least one epi-sulfide group; and initiating polymerization of the compound or mixture of two or more different compounds each containing at least one epi-sulfide group by performing one or more of: i) passing a current through the device; ii) conducting an initial charging cycle; iii) adding an anionic nucleophile; or iv) adding an initiator.

(a-c) 1.0 M LiTFSI DOL:DME:$G_1S$ (30:30:40)+2 wt % $SG_xS$ and (d-f) SOA liquid electrolyte 1.0 M LiTFSI DOL:DME (50:50) after 5 cycles, according to the examples.

Figure 7:
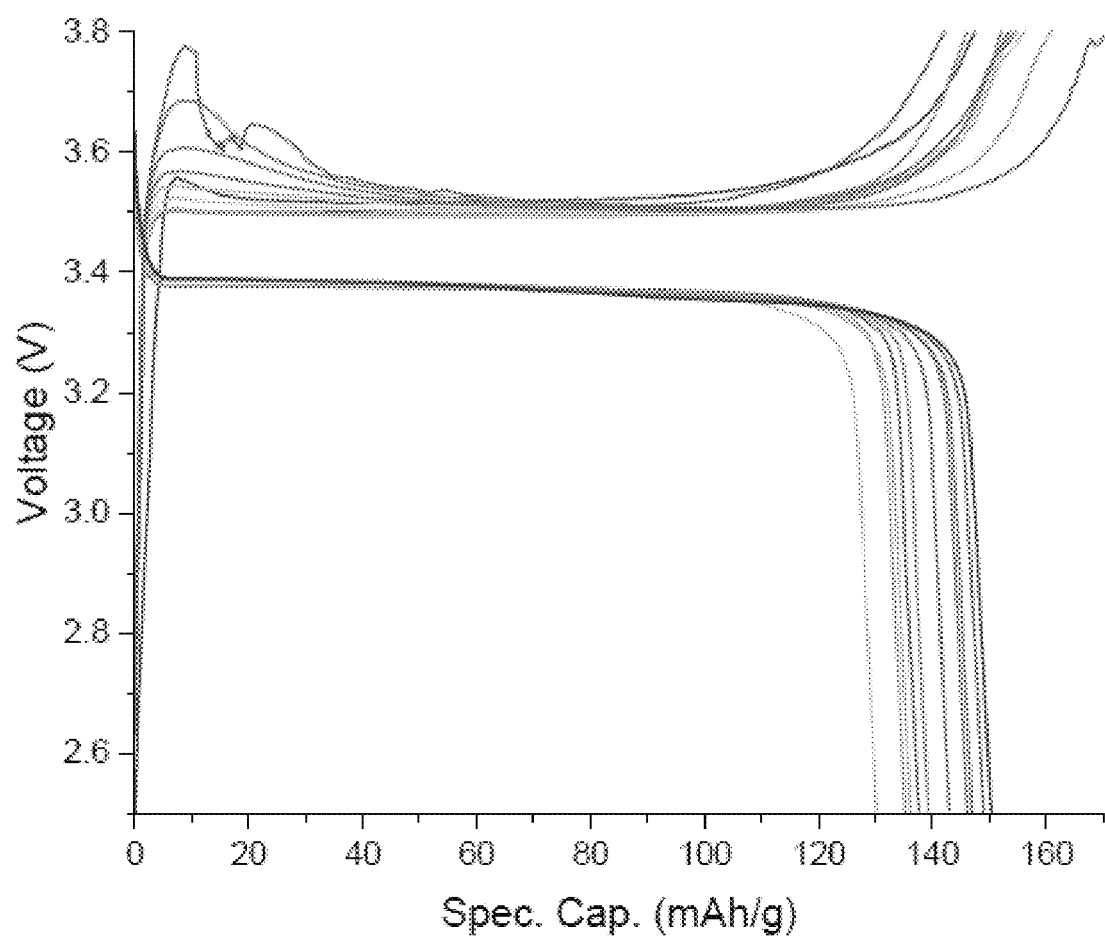

FIG. 7 is a graph of cycling voltage v. specific capacity for a non-sulfur based cell, according to the examples.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As utilized herein with respect to numerical ranges, the terms "approximately," "about," "substantially," and similar terms will be understood by persons of ordinary skill in the art and will vary to some extent depending upon the context in which it is used. If there are uses of the terms that are not clear to persons of ordinary skill in the art, given the context in which it is used, the terms will be plus or minus 10% of the disclosed values. When "approximately," "about," "substantially," and similar terms are applied to a structural feature (e.g., to describe its shape, size, orientation, direction, etc.), these terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, ether, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=$CH_2$, C=$CH_2$, or C=$CHCH_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups.

The phrase "aryl groups" includes groups containing fused rings, such as fused aromatic-aliphatic ring systems (e.g., indanyl, tetrahydronaphthyl, and the like). Aryl groups may be substituted or unsubstituted.

The use of solid polymer electrolytes has previously proven to be an effective approach to address the lithium polysulfide dissolution and high electrode interfacial impedance of Li—S batteries via an in situ polymerization process. However, the conventional in situ synthesis employs a cationic ring-opening polymerization (CROP) of 1,3-dioxolane (DOL) catalyzed by a strong Lewis acid. New polymerization chemistry that is more compatible with Li—S chemistry needs to be developed to mitigate the disadvantages associated with the CROP process. Herein we report a new approach to in situ polymerize a set of new episulfide monomers in solution with LiTFSI salt via an anionic ring-opening polymerization (AROP). This new polymer system takes advantage of the inherent cell chemistry present in the Li—S cell through the nucleophilic lithium sulfides that are generated during the initial discharge cycle and act as the initiator for the polymerization. Their presence was shown to initiate the monomer solvents through AROP with no need for additional catalysts, rather than the more commonly utilized cationic systems, which requires an external Lewis acid catalyst. This work offers an important pathway toward in situ polymer electrolytes for Li—S batteries and offers a new avenue of exploration for polymer electrolyte synthesis. However, this pathway is not limited to only Li—S batteries, and it may be applied to other systems as well.

Lithium-sulfur (Li—S) batteries have given great promise to eventually overtake existing state-of-the-art lithium-ion batteries due to the high theoretical capacity of sulfur, 1675 mAh·g$^{-1}$.[1] Elemental sulfur is an abundant element in the Earth's crust and is currently at a surplus as a result of the purification of natural gas and oil resulting in large amounts of sulfur as a by-product.[2,3] Unfortunately, batteries using lithium-sulfur chemistries remain to be fully realized in large industrial applications due to a number of remaining fatal flaws in the operation of sulfur-based cathode systems. This largely arises from the high solubility of intermediary lithium polysulfide species generated during the charge/discharge of the cathode, which are highly soluble in traditional ether-based liquid electrolytes. One commonly used solution is to replace the liquid electrolyte completely with a polymer-based electrolyte to improve the safety of the batteries.[4] Stacking of polymer electrolytes and electrode layers presents a number of unresolved issues, including interfacial contact between the electrolyte and the electrodes.[4-7]

In the past several years, a number of groups have begun to resolve this issue by forming a polymer portion in situ through polymerization of part of the electrolyte composition,[8-13] or ex situ through reverse vulcanization.[14-16] One method includes the polymerization of 1,3-dioxolane (DOL) via a Lewis acid catalyzed cation ring-opening polymerization (CROP) either through the degradation of $PF_6^-$ anions (release of HF and $PF_5$) or through the addition of an external Lewis acid such as $AlI_3$ or $Al(OTf)_3$ (OTf is a trifluoromethanesulfonate, or "triflate" group) into the electrolyte formulation.[17-24] However, the propagating polymer chains in CROP systems are known to be a cyclic oxonium species as shown in Scheme 1 that are susceptible to nucleophilic attack. The presence of any species more nucleophilic than the monomer results in termination of the living polymer chains rather than in continued propagation of the live polymer.[25,26] This fact has gone largely ignored by the Li—S battery community employing in situ polymerization systems despite the fact that the in situ polymerization is often times reported as occurring in lithium-sulfur batteries that exhibits lithium polysulfides ($Li_2S_x$, x=2,4,6, 8), which are well known for their high nucleophilicity and incompatibility with electrophilic species such as ethylene carbonate and diethyl carbonate-based solvents.[27,28] This presents difficulties in developing in situ polymerizable electrolyte systems that progress through CROP as it must ensure no $Li_2S_x$ species are generated prior to the completion of the polymerization to avoid premature termination.

Scheme 1

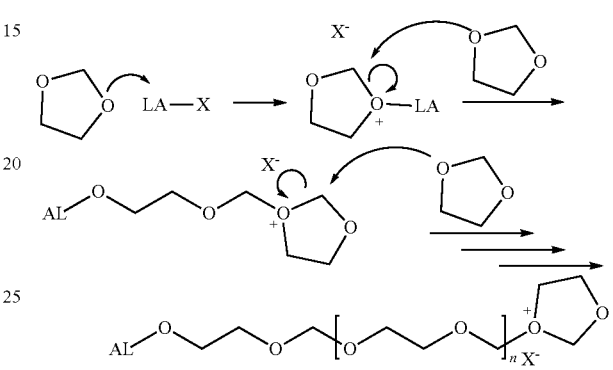

*LA (reversed as AL in some compounds of Schemes 1 and 2) is a Lewis Acid

It has now been found that the pitfalls of CROP may be avoided using anionic ring-opening polymerization (AROP). Unlike CROP systems, AROP is initiated by a nucleophile (Lewis base) and bares a non-cyclic and less sensitive anionic species as the active polymer end.[25] Accordingly, AROP is mechanistically compatible with the environment present in lithium-based batteries such as Li-ion, Li-metal, Li—S, and Li—$O_2$ that require a solid-electrolyte interface (SEI) layer composed of a number of potentially nucleophilic compounds (e.g. $Li_2CO_3$, LiF, $LiOCO_2C_2H_5$, LiOR, where R is H, alkyl, or aryl) through the degradation of electrolyte solvent and salts during the formation cycles.[29] Specifically, nucleophilic lithium sulfides ($S_x^{2-}$) species (a Lewis base) are formed as a discharge product from sulfur electrodes in a Li—S battery. The presence of this species can then be utilized as the initiator for AROP as illustrated in Scheme 2.

Scheme 2

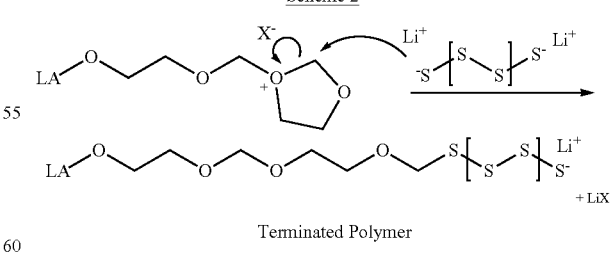

Terminated Polymer

However, the AROP systems described herein exploit the presence of $Li_2S_x$ species in the electrolytes to prepare solid polymer electrolytes, where the polymerization is initiated by the $Li_2S_x$ species. A proposed mechanism for the reaction is presented in Scheme 3 (y=0, 1, or 2, m=1-3, and n=degree of polymerization (DP)).

Scheme 3

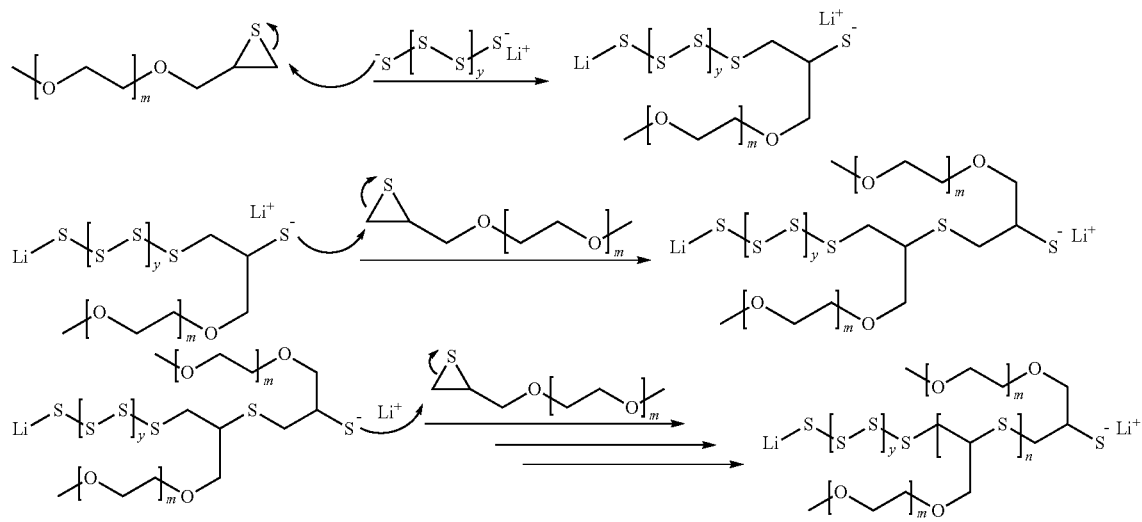

In one aspect, a new solid polymer electrolyte (SPE) for solid-state electrochemical energy storage applications is provided. The precursors for the SPE formation can be filled to the cell just like a liquid electrolyte and the polymerized in situ. This warrants the intimate contact of the electrolyte with active electrode materials. However, during the initial electrochemical operation, the liquid precursors will be catalyzed by the trace amount of the discharge products and initiated a polymerization reaction. The SPE will be formed in the initial cycle and become an all-solid-state battery. The conductivity of the SPE can be tuned by changing the ratio of the cross linking agent and the monomer and the lithium salt concentration. The low conductivity barrier will be addressed through formation of a gel polymer electrolyte (GPE). As used herein, a "solid-state" electrolyte could be a dry polymer (i.e. without a solvent, i.e. plasticizer) or it may be wetted polymer (i.e. with a solvent, i.e. plasticizer).

Liquid electrolyte solvents, such as DOL and DME, the common electrolyte solvents used in the current Li—S battery, are added to the mixture of the precursors. After polymerization, the added liquid electrolyte solvents will be trapped inside the three-dimensional crosslinked polymer network forming a gel-polymer electrolyte (GPE). This GPE can significantly enhance the conductivity, and improve C-rate or power capability of the solid-state cells. By using an electrolyte system that is completely liquid during cell assembly it has now been shown that a SPE and GPE can be assembled with no additional requirements outside of traditional means.

The present systems include an electrolyte formulation that contains a polymerizable electrolyte solvent, a non-polymerizable solvent (plasticizer), lithium salt, along with other additives to meet the demands of the battery systems. Through generation of nucleophilic anions, initiation of anionic ring-opening polymerization can be achieved, or small quantities of additional additives to initiate the AROMP may be used to polymerize the electrolyte components once the cell has been assembled. This allows for assembly of the electrochemical cells in a manner identical to traditional liquid electrolytes, allowing for all pores of the electrodes are filled with electrolyte (wetted). After this occurs, the electrolyte is solidified through the above polymerization. Illustrative, polymerizable electrolyte solvents that we have begun to employ in battery cells for this purpose include, but are not limited to ethylene sulfide (ES), propylene sulfide (PS), methoxymethyl thiirane (MeOES), ethoxymethyl thiirane (EtOES), isopropoxymethyl thiirane (iPrOES), (2-methoxyethoxy)methyl thiirane ($G_1S$), and 1,2-bis(2,3-epithipropoxy) ethane (SG1S). Structurally, these compounds are:

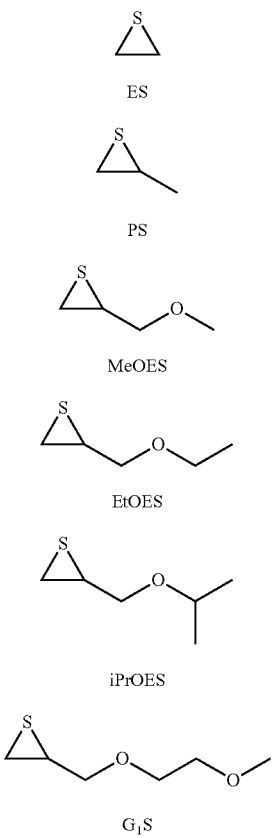

-continued

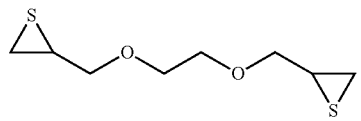 [SMILES: C(COCC1CS1)OCC1CS1]

SG₁S

The initiating species in the polymerization of the above monomers is based upon the components present in Li—S battery chemistry as intermediary discharge products between the fully oxidized and reduced forms of $S_8$ and $Li_2S$, including a number of highly soluble polysulfides, $Li_2S_x$ (x=8, 6, 4, and 2). The solubility and nucleophilic nature of these intermediary highly soluble polysulfides, has traditionally been problematic, however, the reactions presented herein, take advantage of their presence and sequester them due to the reaction with the polymerizable epi-sulfide monomers.

As an illustration of the process where a lithium polysulfide provides the polymerization initiation, Scheme 4 is provided.

Scheme 4

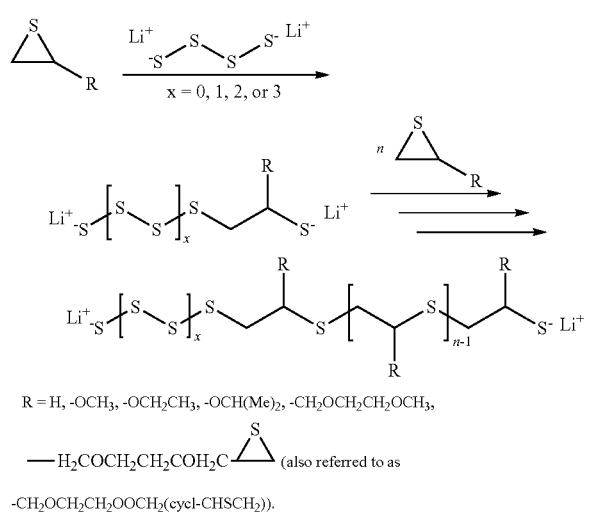

R = H, -OCH₃, -OCH₂CH₃, -OCH(Me)₂, -CH₂OCH₂CH₂OCH₃,

—H₂COCH₂CH₂COH₂C⎯△S (also referred to as

-CH₂OCH₂CH₂OOCH₂(cycl-CHSCH₂)).

Scheme 5

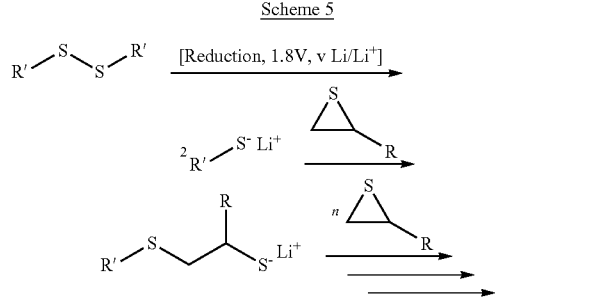

-continued

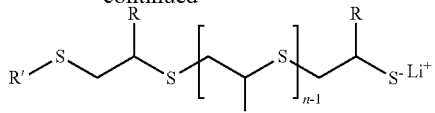

R = H, -OCH₃, OCH₂CH₃, -OCH(Me)₂, -CH₂OCH₂CH₂OCH₃,

—H₂COCH₂CH₂COH₂C⎯△S (also referred to as

-CH₂OCH₂CH₂OCH₂(cycl-CHSCH₂)); and

R' = -CH₃, -CH₂CH₂CH₃, -CH₂CH = CH₂.

Above Schemes 4 and S are an illustration of an in-situ polymerization through nucleophilic attack of: Scheme 1) lithium polysulfide in Li—S batteries and Scheme 2) organic lithium sulfide in non-sulfur batteries (Li-ion and Li-metal) to generate in situ polythioether electrolytes.

In one aspect, a battery is provided that includes a cathode having a cathode active material, an anode including lithium, and an electrolyte having an aprotic solvent, a lithium salt, and a compound or mixture of two or more different compounds each having at least one epi-sulfide group. As used herein, the term "epi-sulfide" describes materials having a thio-epoxide functionality. In some embodiments, the electrolyte includes the mixture of two or more different compounds each containing at least one epi-sulfide group.

The batteries described herein may include where each of the compound or mixture of two or more different compounds each contain at least one epi-sulfide group. The epi-sulfide compound may, therefore, be represented as [epi-sulfide]$_p$-[L]$_{p'}$-[epi-sulfide]$_{p''}$, wherein p is at least 1, p' is at least one, and p' is 0 or greater, and each L is a linker where p" is greater than 0 or is a terminal group when p" is 0. In such embodiments, linker L may be a alkyl, ether, polyether, aryl, heteroaryl, or heterocyclyl. The compound may also, according to various embodiments, be an oligomer having two or more epi-sulfide groups. For example, p may be greater than 1, or p" may be greater than 1, or p and p" may be 1 or greater.

In other embodiments, the compound or mixture of two or more different compounds each containing at least one epi-sulfide group may be represented by Formula I:

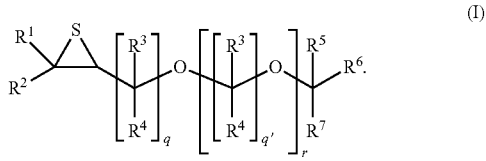

(I)

In Formula I, each $R^1$, $R^2$, $R^3$, $R^4$, $R^5$, $R^6$, and $R^7$ may be individually H, alkyl, alkoxy, aryl, aralkyl, heteroaryl, heteroaralkyl, heterocyclylalkoxyl, heterocyclyl, or heterocyclylalkyl; q may be 0, 1, 2, or 3; q' may be 1, 2, 3, or 4; and r may be at least 1. In some embodiments, $R^1$, $R^2$, $R^3$, $R^4$, $R^5$, and $R^7$ may be H or alkyl, $R^6$ may be H, alkyl or

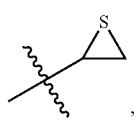 [SMILES: *C1CS1]

q may be 1 or 2, q' may be 1 or 2, and r may be 0, 1, or 2. In any of the embodiments, herein the electrolyte may include a mixture of two or more different compounds of Formula I.

As noted above the electrolytes described herein may include two or compounds of Formula I. In some embodiments, these may be represented as Formulae IA and IB:

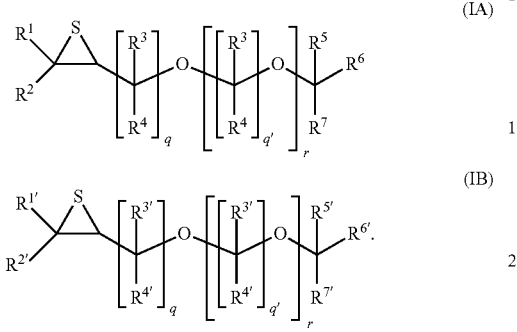

In Formulae IA and IB, each $R^1$, $R^2$, $R^3$, $R^4$, $R^5$, $R^6$, and $R^7$ may be individually H, alkyl, alkoxy, aryl, aralkyl, heteroaryl, heteroaralkyl, heterocyclylalkoxyl, heterocyclyl, or heterocyclylalkyl; each $R^{1'}$, $R^{2'}$, $R^{3'}$, $R^{4'}$, $R^{5'}$, $R^{6'}$, and $R^{7'}$ may be individually H, alkyl, alkoxy, aryl, aralkyl, heteroaryl, heteroaralkyl, heterocyclylalkoxyl, heterocyclyl, or heterocyclylalkyl, with the proviso that at least one $R^{1'}$, $R^{2'}$, $R^{3'}$, $R^{4'}$, $R^{5'}$, $R^{6'}$, and $R^{7'}$ contains a heterocyclyl group; each q may be individually 0, 1, 2, or 3; each q' may be individually 1, 2, 3, or 4; and each r individually may at least 1. In various embodiments, each $R^1$, $R^2$, $R^3$, $R^4$, $R^5$, $R^6$, and $R^7$ may be individually H or alkyl; each q may be individually 1 or 2; each q' may be individually 1 or 2; each r may be individually 0, 1, or 2; and each $R^{1'}$, $R^{2'}$, $R^{3'}$, $R^{4'}$, $R^{5'}$, and $R^{6'}$ individually may be H or alkyl, and $R^{7'}$ may be heterocyclyl. In any embodiments herein, each $R^1$, $R^2$, $R^3$, $R^4$, $R^5$, $R^6$, and $R^7$ may be individually H or alkyl; each q may be individually 1 or 2; each q' may be individually 1 or 2; each r may be individually 0, 1, or 2; each $R^{1'}$, $R^{2'}$, $R^{3'}$, $R^{4'}$, $R^{5'}$, and $R^{6'}$ individually may be H or alkyl; and $R^{7'}$ may be

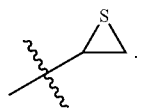

In any embodiments herein, each $R^1$, $R^2$, $R^3$, $R^4$, $R^5$, $R^6$, and $R^7$ may be H; each q may be individually 1 or 2; each q' may be individually 1 or 2; each r may be individually 0, 1, or 2; $R^{1'}$, $R^{2'}$, $R^{3'}$, $R^{1'}$, $R^{5'}$, and $R^{6'}$ may be H; and $R^{7'}$ may be

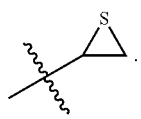 [SMILES: *C1CS1]

As illustrative examples of the compounds of Formula IA and IB, the compound of Formula IA may be $G_1S$, and the compound of Formula (IB) may be $SG_xS$:

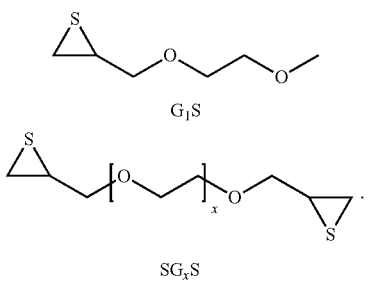

The amount of the epi-sulfide, or epi-sulfides, in the electrolyte may vary depending on the degree of gelation and solidification needed for the solid-state electrolyte. For example, the epi-sulfide, where generally described or as that of Formula I, IA, or IB, may be from about 80 wt % of the electrolyte to about 10 wt %.

The battery may be a lithium ion battery. In some embodiments, the cathode active material comprises sulfur. In other embodiments, the cathode active material comprises sulfur, NMC 111, NMC532, NMC622, NMC811, $LiNiO_2$, NCA, $LiNi_{0.5}Mn_{1.5}O_4$, $LiFePO_4$, or $LiMn_2O_4$.

The cathode of the battery may include other materials and additives such as, but not limited to, a current collector, binder, or conductive carbon species. Illustrative conductive carbon materials include, but are not limited to, synthetic graphite, natural graphite, expanded graphite, graphene, reduced graphene oxide, a metal-organic framework, amorphous carbon, hard carbon, soft carbon, carbon black, acetylene black, carbon spheres, mesocarbon microbeads (MCMB), mesoporous carbon, porous carbon matrix, carbon nanofiber, carbon aerogel, single-walled carbon nanotubes, multi-walled carbon nanotubes, carbon nanotube arrays, and any mixture of two or more thereof. In some embodiments, the conductive carbon materials include, microporous carbon, mesoporous carbon, mesoporous microbeads, graphite, expandable graphite, carbon black, or carbon nanotubes, or any combination thereof. Commercial examples of carbon black include, but are not limited to, Super P, Black Pearls® 2000, Denka Black, Vulcan XC72R, and Ketjen Black®.

The binder may be present in the anodes in an amount of from about 0.1 wt % to about 99 wt %. In some embodiments, the binder is present in the electrode in an amount of from about 5 wt % to about 20 wt %. Illustrative binders include, but are not limited to, polyvinylidene fluoride (PVDF), polyvinyl alcohol (PVA), polyethylene, polystyrene, polyethylene oxide, polytetrafluoroethylene (Teflon), polyacrylonitrile, polyimide, styrene butadiene rubber (SBR), carboxy methyl cellulose (CMC), gelatine, sodium alginate, polythiophene, polyacetylene, poly(9,9-dioctylfluorene-co-fluorenone), poly(9,9-dioctylfluorene-co-fluorenone-co-methylbenzoic ester), a copolymer of any two or more such polymers, and a blend of any two or more such polymers. In some embodiments, the binder is an electrically conductive polymer such as, but not limited to, polythiophene, polyacetylene, poly(9,9-dioctylfluorene-co-fluorenone), poly(9,9-dioctylfluorene-co-fluorenone-co-methylbenzoic ester), and a copolymer of any two or more such conductive polymers.

The cathode current collector may be prepared from a wide variety of materials. For example, illustrative current collectors include, but are not limited to, copper, stainless steel, titanium, tantalum, platinum, palladium, gold, silver, iron, aluminum, nickel, rhodium, manganese, vanadium, titanium, tungsten, cobalt nickel alloy, highly alloyed ferritic stainless steel containing molybdenum and chromium; or nickel-, chromium-, or molybdenum-containing alloys, or a carbon-coated metal described above. The current collector may take the form of a foil, mesh, or screen. In some embodiments, the electroactive material disclosed herein and one or more of a conductive carbon material and a binder are contacted with the current collector by casting, pressing, or rolling the mixture thereto. In some embodiments, the current collector is copper, stainless steel, titanium, tantalum, platinum, gold, aluminum, nickel, cobalt, cobalt nickel alloy, highly alloyed ferritic stainless steel containing molybdenum and chromium, a nickel-containing alloy, a chromium-containing alloy, or a molybdenum-containing alloy. Current collectors for the cathode may be made of a wire mesh.

The anode is noted to include lithium. This may be as lithium metal, such as a lithium foil. In some embodiments, the anode includes a lithium foil, lithium mesh, lithium nanoparticles, lithiated carbon, lithiated tin, lithiated silicon, a sodium foil, sodium mesh, sodium nanoparticles, sodiated carbon, sodiated tin, sodiated silicon, a potassium foil, potassium mesh, potassium nanoparticles, potassiated carbon, potassiated tin, potassiated silicon, a magnesium foil, magnesium ribbon, magnesium mesh, magnesium nanoparticles, magnesiated carbon, magnesiated tin, magnesiated silicon, a zinc foil, a zinc ribbon, zinc mesh, zinc nanoparticles, zincated carbon, zincated, tin, zincated silicon, or a combination thereof. In some embodiments, the anode comprises a lithium foil, lithium mesh, lithium nanoparticles, lithiated carbon, lithiated tin, or lithiated silicon. In other embodiments, the anode comprises a lithium foil, lithium mesh, lithium nanoparticles, or a combination thereof. In other embodiments, the anode includes one or more of lithium metal, lithiated carbon, lithiated silicon, lithiated sulfur, lithiated phosphorous, lithiated phosphorene, LiM alloy (where M stands for Na, Al, Bi, Cd, Mg, Sn, and Sb), lithium titanium oxide, sodium metal, sodiated carbon, sodiated silicon, sodiated sulfur, sodiated phosphorous, sodiated phosphorene, NaM alloy (where M stands for Li, Al, Bi, Cd, Mg, Sn, and Sb), sodium titanium oxide, or a combination of any two or more thereof. The electrochemical device may be discharged to about 0.1 V to about 1.3 V, or charged to about 1.3 V to about 4.0 V. The electrochemical device may be discharged at a current density of about 50 μA to about 500 μA, about 100 μA to about 300 μA, or of about 200 μA to about 300 μA.

With regard to the electrolyte, it is noted to include an aprotic solvent and lithium salt in addition to the epi-sulfide compound(s). Illustrative lithium salts include, but are not limited to lithium alkyl fluorophosphates, lithium alkyl fluoroborates, lithium 4,5-dicyano-2-(trifluoromethyl) imidazole, lithium 4,5-dicyano-2-methylimidazole, trilithium 2,2',2''-tris(trifluoromethyl)benzotris(imidazolate); LiN(CN)$_2$; Li(CF$_3$CO$_2$); Li(C$_2$F$_5$CO$_2$); LiCF$_3$SO$_3$; LiCH$_3$SO$_3$; LiN(SO$_2$CF$_3$)$_2$; LiN(SO$_2$F)$_2$; LiC(CF$_3$SO$_2$)$_3$; LiN(SO$_2$C$_2$F$_5$)$_2$; LiClO$_4$; LiBF$_4$; LiAsF$_6$; LiPF$_6$; LiBF$_2$(C$_2$O$_4$), LiB(C$_2$O$_4$)$_2$, LiPF$_2$(C$_2$O$_4$)$_2$, LiPF$_4$(C$_2$O$_4$), LiAsF$_6$, LiF, LiCl, LiBr, LiN(SO$_2$CF$_3$)$_2$, LiN(SO$_2$F)$_2$, Li$_2$(B$_{12}$X$_{12-p}$H$_p$); Li$_2$(B$_{10}$X$_{10-p'}$H$_{p'}$); or a mixture of any two or more thereof, wherein X may be independently at each occurrence a halogen, p may be 0, 1, 2, 3, 4, 5, 6, 7, 8, 9, 10, 11, or 12, and p' may be 0, 1, 2, 3, 4, 5, 6, 7, 8, 9, or 10. It should be noted that for those lithium salts specifically called out above, the lithium may alternatively be replaced 1:1, or mixed with, Na or K. In some embodiments, illustrative salts for use in the electrolytes include, but are not limited to, lithium salts such as LiCF$_3$CO$_2$, LiC$_2$F$_5$CO$_2$, LiClO$_4$, LiBF$_4$, LiAsF$_6$, LiPF$_6$, LiPF$_2$(C$_2$O$_4$)$_2$, LiPF$_4$C$_2$O$_4$, LiCF$_3$SO$_3$, LiN(CF$_3$SO$_2$)$_2$, LiC(CF$_3$SO$_2$)$_3$, LiN(SO$_2$C$_2$F$_5$)$_2$), lithium alkyl fluorophosphates, Li(C$_2$O$_4$)$_2$, LiBF$_2$C$_2$O$_4$, Li$_2$B$_{12}$X$_{12}$-pHp, Li$_2$B$_{10}$X$_{10}$-yHy, or a mixture of any two or more lithium salts, where X is OH, F, Cl, or Br; p is 0, 1, 2, 3, 4, 5, 6, 7, 8, 9, 10, 11, or 12; and y is 0, 1, 2, 3, 4, 5, 6, 7, 8, 9, or 10. The concentration of the salt may be from about 0.1M to about 5M. This may include from about 0.1 M to about 2M, from about 0.5 M to about 2M, or about 1 M.

Illustrative aprotic solvents include, but are not limited to, but are not limited to ethylene carbonate, dimethyl carbonate, ethyl methyl carbonate, diethyl carbonate, propylene carbonate, fluorinated carbonates, fluoroethylene carbonate, 4-(trifluoromethyl)-1,3-dioxolan-2-one, propylene carbonate, dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, trifluoroethyl ethyl carbonate, heptafluoropropyl ethyl carbonate, hexafluoroisopropyl methyl carbonate, pentafluoroethyl ethyl carbonate, pentafluorobutyl methyl carbonate, pentafluorobutyl ethyl carbonate, dimethoxyethane, triglyme, dimethyl ether, diglyme, tetraglyme, dimethyl ethylene carbonate, ethyl acetate, trifluoroethyl acetate, ethyl methyl sulfone, sulfolane, methyl isopropyl sulfone, butyrolactone, acetonitrile, succinonitrile, methyl 2-cyanoacetate, N,N-dimethylacetamide, 2,2,2-trifluoro-N,N-dimethylacetamide, methyl dimethylcarbamate, 2,2,2-trifluoroethyl dimethylcarbamate, or a mixture of any two or more thereof. Other solvents that may be used in the electrolytes include, but are not limited to, organic sulfates, esters, cyclic esters, fluorinated esters, nitriles, amides, dinitriles, fluorinated amides, carbamates, fluorinated carbamates, cyanoester compounds, and ionic liquid such as pyrrolidinium-based ionic liquids, piperidinium-based ionic liquids, imidazolium-based ionic liquids, ammonium-based ionic liquids, phosphonium-based ionic liquids, cyclic phosphonium-based ionic liquids, and sulfonium-based ionic liquids. In some embodiments, the solvents are ether-based solvents. Illustrative ether-based solvents include, but are not limited to 1,3-dioxolane ("DOL"), dimethoxyethane ("DME"), tetrahydrofuran, di(ethylene glycol) dimethyl ether, tri(ethylene glycol) dimethyl ether, diglyme (DGM), partly silanized ether, tetra (ethylene glycol) dimethyl ether ("TEGDME"), poly(ethylene glycol) dimethyl ether (PEGDME), (2,2,2-trifluoroethyl) carbonate (FEMC), 1,4-dioxane, 1,1,2,2-tetrafluoroethyl-2,2,3,3-tetrafluoropropyl ether; 1,1,2,2-tetrafluoroethyl-2,2,3,3,3-pentafluoropropyl ether; 2,2,2-trisfluoroethyl-1,1,2,3,3,3-hexafluoropropyl ether; ethyl-1,1,2,3,3,3-hexafluoropropyl ether; difluoromethyl-2,2,3,3,3-pentafluoropropyl ether; difluoromethyl-2,2,3,3-tetrafluoropropyl ether; 2-fluoro-1,3-dioxolane; 2,2-difluoro-1,3-dioxolane; 2-trifluoromethyl-1,3-dioxolane; 2,2-bis(trifluoromethyl)-1,3-dioxolane; 4-fluoro-1,3-dioxolane; 4,5-difluoro-1,3-dioxolane, or a mixture of any two or more. In some embodiments, the solvents may be carbonated-based solvents, ether-based solvents, fluorinated ether-based solvents, dimethyl sulfoxide, sulfone, ionic liquids, or a mixture of any two or more thereof.

In some embodiments, the aprotic solvents are non-fluorinated, non-aqueous solvents. Illustrative non-fluorinated, non-aqueous solvents include, but are not limited to, ethylene carbonate, dimethyl carbonate, ethyl methyl carbonate, diethyl carbonate, propylene carbonate, fluorinated carbonate, or a mixture of any two or more thereof. In some embodiments, the co-solvents are ether-based solvents. Illustrative ether-based co-solvents include, but are not limited to, 1,3-dioxolane ("DOL"), dimethoxyethane ("DME"), tetrahydrofuran, di(ethylene glycol) dimethyl ether, tri (ethylene glycol) dimethyl ether, diglyme (DGM), partly silanized ether, tetra(ethylene glycol) dimethyl ether ("TEGDME"), poly(ethylene glycol) dimethyl ether (PEGDME), 1,4-dioxane, or a mixture of any two or more thereof.

In another aspect, a method of forming a gelled electrolyte is provided. Such methods include providing a battery or battery housing that includes a cathode comprising a cathode active material and an anode comprising lithium, and adding an electrolyte that includes an aprotic solvent, a lithium salt, and a compound or mixture of two or more different compounds each containing at least one epi-sulfide group, followed by initiating polymerization of the compound or mixture of two or more different compounds each containing at least one epi-sulfide group. The initiation of the polymerization may be via one or more of i) passing a current through the device, ii) conducting an initial charging cycle, iii) adding an anionic nucleophile, or iv) adding an initiator. The epi-sulfide may be any of the compounds as described herein either generally, or with reference to Formulae I, IA, and/or IB. Upon gelation (i.e. polymerization) of the electrolyte and the epi-sulfide compound or compounds, the electrolyte may be considered as a solid-state electrolyte, which depending on the degree of polymerization and cross-linking among the epi-sulfide groups or other polymerizable functionality within the compounds, may have varying degrees of solidification as exhibited by hardness or mechanical strength.

In such methods, the initiating of the polymerization may include performing a charging cycle to a voltage greater than 0.1 V. In some embodiments, this includes performing a charging cycle to a voltage ranging from about 0.1 V to about 6 V. In some embodiments, the method includes a voltage hold, typically from greater than 0.0 V to about 2.0 V, where the current is not controlled but is measured. The initiation is stopped when the measured current drops below a certain threshold. The threshold may be less than C/20 for the cell.

As noted above, an anionic nucleophile may be used to initiate polymerization of the epi-sulfide compounds. This may be included in the method by incorporating the anionic nucleophile in the electrolyte and then initiating the reaction thermally or electronically. Illustrative anionic nucleophiles include, but are not limited to, material such as $M_2CO_3$, MF, $MOCO_2C_2H_5$, MOR, wherein M is Li, Na, or K, and R is H, alkyl, aryl.

In addition to, or in place of the anionic nucleophile, other initiators may be used in the method as well. Such other initiators may include a compound or mixture of compounds of formula $R^{30}$—S—S—$R^{31}$, wherein $R^{30}$ and $R^{31}$ are each individually alkyl, cycloalkyl, cycloalkylalkyl, aryl, aralkyl, heterocyclyl, heterocyclylalkyl, heteroaryl, or heteroaralkyl. In some embodiments, $R^{30}$ and $R^{31}$ are each individually $C_{1-12}$ alkyl. In other embodiments, $R^{30}$ and $R^{31}$ are each individually methyl, ethyl, or allyl. Illustrative initiators include, but are not limited to, dimethyldisulfide (DMDS), diethyl disulfide (DEDS), diallyl disulfide (DADS), or a mixture of any two or more thereof. The amount of initiator, no matter which one or mixture is chosen, may range from about 0.1 mM to 0.5 M in the electrolyte. This can include from about 0.1 mM to about 0.1 M, or from 0.1 mM to about 10 mM.

The battery with the solid-state electrolyte that is produced by the methods, a lithium ion battery. In some embodiments, the cathode active material comprises sulfur. In other embodiments, the cathode active material comprises sulfur, NMC 111, NMC532, NMC622, NMC811, $LiNiO_2$, NCA, $LiNi_{0.5}Mn_{1.5}O_4$, $LiFePO_4$, or $LiMn_2O_4$.

In a further aspect, an electrolyte for a Li—S battery is provided. The electrolyte is as described above with regard to including an aprotic solvent, a lithium salt, and a compound of Formula (I) (prior to polymerization) or the polymerization product of the compound of Formula (I) (i.e. after polymerization). The compound of Formula I is:

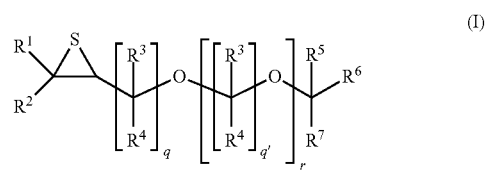

wherein each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl; q is 0, 1, 2, or 3; q' is 1, 2, 3, or 4; and r is at least 1. Other embodiments of the compound of Formula I are as described above with references to the R groups and the substructures of Formulae IA and IB.

In a yet further aspect, a compound of Formula I is provided:

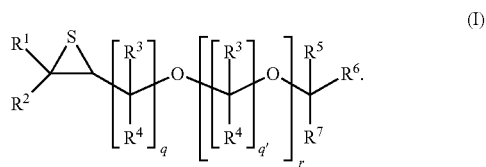

In Formula I, each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl; q is 0, 1, 2, or 3; q' is 1, 2, 3, or 4; and r is at least 1. Other embodiments of the compound of Formula I are as described above with references to the R groups and the substructures of Formulae IA and IB. Illustrative compounds of Formula I include, but are not limited to, $G_1S$ and $SG_xS$:

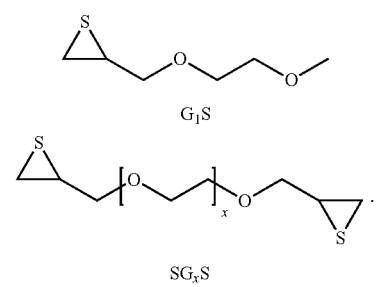

The present invention, thus generally described, will be understood more readily by reference to the following examples, which are provided by way of illustration and are not intended to be limiting of the present invention.

Examples

Materials and Methods. 1,3-dioxolane (DOL, 99% of an approximate 75 ppm BHT), 1,2-dimethoxyethane (DME, 99.9% HPLC grade), lithium bis(trifluoromethyl sulfonyl) imide (LiTFSI, 99.98%), sodium hydride (NaH, 90%, dry powder), tetrahydrofuran (THF, 99.9%, anhydrous), ethylene glycol diglycidyl ether mixture (TCI), methanol (99.9%), thiourea (99.0%), sulfur (99.99%), and lithium sulfide (99.98%) were acquired from Sigma-Aldrich; Silica gel (230-400 mesh, grade 60) and diethyl ether (ACS grade) were acquired from Thermo-Fischer Scientific; Epichlorohydrin (99%, anhydrous) and 2-methoxyethanol (99%) were acquired from Acros Organics; Sodium sulfate ($Na_2SO_4$, anhydrous, ACS grade) was purchased from VWR (BDH).

All electrolyte solvents were distilled by short-path distillation. Episulfides $G_1S$, $SG_xS$, and DOL were dried over $CaH_2$ for >48 h and then passed through a 0.2 µm filter before use. DME was dried over 4 Å molecular sieves. LiTFSI was dried at 125° C. under a high vacuum for 24 h. $G_1S$ and $SG_xS$ were stored in the freezer at −10° C. in an argon-filled glovebox to ensure stability over extended periods with no signs of premature polymerization after several months.

Water content was determined by Karl-Fischer titration using a Mettler-Toledo C30 Coulometric Titrator using Reagent E.

All electrolytes were prepared in a glovebox by weighing the appropriate LiTFSI mass and then dissolving it in 0.5 mL of electrolyte solvent. This solution was then diluted to 1.0 mL to provide exact molar concentrations. From this solution, 0.25 mL was removed and weighed and then cross-linker ($SG_xS$) was added as a function of wt %. All electrolytes containing episulfides were either used immediately or stored in the glovebox freezer at −10° C. after formulation to reduce the chance of premature polymerization.

Ex situ polymerizations were performed in vacuum dried glass sample vials by preparing 0.5 mL of electrolyte as described above. 2 µL of 0.2 M $Li_2S_6$ in DME was added to the electrolyte solution with stirring. This solution was allowed to rest at ambient temperature in the glovebox without stirring for 5 h to ensure full polymerization.

Electrode Preparation. Sulfurized-polyacrylonitrile (SPAN) cathodes were cut into discs with a diameter of 15 mm. Sulfur loading was 1.5 mg/cm².

Electrochemical Testing. 2032-coin cells were assembled in an argon filled glovebox with lithium foil as the anode and SPAN as the cathode. Solupor 7PO3A (diameter=16 mm) was used as the separator and the liquid monomer electrolyte was kept at a constant volume of 40 µL per cell (E/S=15 µL/mg). Cell cycling was conducted using a Maccor series 4000 battery cycler at constant current determined by active material loading in the cathode. Charge steps for Li—S cells were set to terminate either through voltage cutoff mode (3.0 V) or capacity cutoff at ×1.5 the previous discharge step.

Electrochemical impedance spectroscopy (EIS) was performed using a Solartron Analytical 1400 Cell Test System from 1.0 MHz to 0.1 Hz at OCV. Bulk ionic conductivity of monomer electrolytes and polymer electrolytes were evaluated using a stainless-steel coin cell assembly with a PTFE washer filled with electrolyte. Polymer electrolytes were prepared by the addition of 1 µL of 0.25 M $Li_2S_x$ in DME (x~6, final $[S_x^{2-}]$=2 mM) before assembly, this was allowed to rest at ambient conditions for 1 week prior to EIS testing. The PTFE washer dimensions were set at 0.177 cm thickness (l) and 0.502 cm² internal area ($\pi r^2$). EIS was used to determine the Ohm resistance ($R_\Omega$) from the highest frequency Z' intercept that was used with Equation 1 to determine the bulk ionic conductivity (σ) of the electrolyte.

$$\sigma = \frac{l}{\pi r^2 \cdot R_\Omega} \cdot 1000 \qquad [1]$$

Conductivity was determined for temperatures within the range of 0-60° C. at every 10° C. for polymerized electrolytes, allowing the samples the temperature acclimate for at least 10 min after reaching the set value. Monomer electrolyte conductivity was determined only at ambient temperature. For each sample and temperature, the EIS measurement was conducted in triplicate and the conductivity determined for each measurement prior to statistical analysis.

Cyclic voltammetry (CV) was conducted using a Gamry Potentiostat Reference 600+ inside an argon-filled glovebox. Lithium electrodes were prepared by attaching fresh lithium foil to a glass electrode with an internal copper wire. The platinum (working) and lithium (counter and reference) electrodes were immersed in a vial containing 1.0 mL of electrolyte solution. The voltage was swept from −0.5 V to either 3.0 V or 5.0 V vs Li*/Li starting at OCV three times with a scan rate of 10 mV/s.

Post-test Analysis. Li—S cells were prepared and cycled for 5 cycles before being stopped and cell parts harvested for analysis. After de-crimping the cell stacks were separated. Samples bound for SEM were each washed twice with 300 µL of fresh DOL and allowed to dry for several minutes under an argon atmosphere before being transferred in an air-tight container to the instrument for mounting. Samples were mounted quickly on SEM mounts in open air and then immediately transferred into the instrument's vacuum chamber.

Cell parts used for NMR analysis were not pre-washed but were rather transferred out of the glovebox neat after removal of the lithium chip. These cell parts were set stirring in a sealed vial containing 3 mL of DCM with 3 drops of $H_2O$ over 1 week to dissolve the polymer electrolyte (linear polymer). After 1 week, the supernatant was removed and passed through a small pad of $Na_2SO_4$ to dry and solvent removed under reduced pressure. This sample was then subjected to NMR analysis by redissolving in $CDCl_3$ (NMR).

Synthesis of Monomers. Generally, the single step reaction involved in the synthesis of the targets is shown below in Scheme 6.

Scheme 6

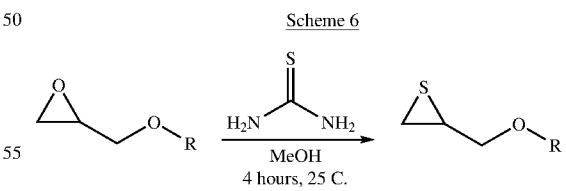

| R-Group | Reaction Yield (%) | Compound |
|---|---|---|
| Me | N/A | MeOES |
| Et | 61.5 | EtOES |
| iPr | 66.0 | iPrOES |
| —$CH_2CH_2OMe$ | 78.4 | $G_1S$ |
| —$[CH_2CH_2O]_x[cycl-CHCH_2S]$ | 29.6 | $SG_1S$ |

Scheme 7:

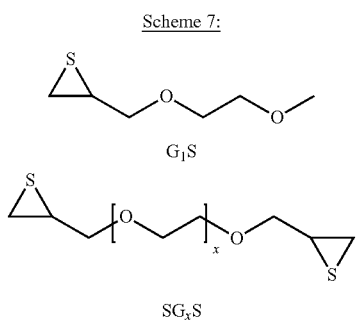

Above is shown Scheme 7, which illustrates the synthesis of episulfide polymerizable electrolyte solvents. Polymerization of a mixture of G1S and SG1S in an applicable electrolyte system (i.e. Scheme 3) in an ex situ setting provided an elastic gel with no signs of salt precipitation even with 1.0 M LiTFSI present within 60 min of initiator addition.

Synthesis of 2-[(2-methoxyethoxy)methyl]oxirane

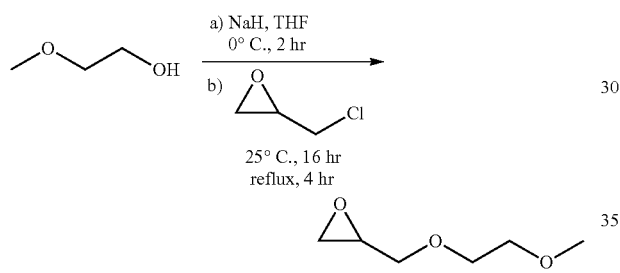

To an oven dried 250 mL flask, sodium hydride (60% in mineral oil, 4.202 g, 105.05 mmol) was added and flushed with dry nitrogen. This was rinsed three times with pentane and the supernatant removed via cannula each time and remaining solid powder dried under vacuum. This was re-suspended in anhydrous THF (80 mL) and cooled to 0° C., at which point 2-methoxyethanol (7.90 mL, 100.2 mmol) was added dropwise while stirring. The resulting mixture was allowed to come to ambient temperature over 2 hours. Finally, epichlorohydrin (7.80 mL, 99.7 mmol) was added portion wise and the mixture was then allowed to stir at ambient temperature under nitrogen for 16 hours. The reaction mixture was then refluxed for 4 hours, cooled to ambient temperature, and then filtered through a pad of Celite 545 (15 cm). Following this, the filtrate was concentrated under reduced pressure to give the crude reaction mixture as a clear-orange liquid. This was purified by fractional short-path vacuum distillation at 12 kPa from 92.0-94.0° C. to give the target compound as a clear-colorless liquid in 25.7% yield (3.3919 g, 25.67 mmol). $^1$H NMR (300 MHz, CDCl$_3$): δ/ppm 3.80 (dd, J=11.7, 3.0 Hz, 1H), 3.74-3.41 (m, 5H), 3.38 (s, 3H), 3.20-3.15 (m, 1H), 2.80 (d, J=4.2 Hz, 0.5H) 2.79 (d, J=4.1 Hz, 0.5H), 2.61 (d, J=2.7 Hz, 0.5H), 2.60 (d, J=2.7 Hz, 0.5H); $^{13}$C NMR (70 MHz, CDCl$_3$): δ/ppm 72.22, 72.02, 70.76, 59.23, 50.96, 44.41; GC-MS m/z (% relative intensity, ion): 131.0 (M$^+$, 0.3), 87.0 (CH$_2$OCHCH$_2$OCH$_2$$^+$, 16), 73.0 (CH$_2$OCHCH$_2$ O$^{·+}$, 21), 59.0 (CH$_3$OCH$_2$CH$_2$$^+$, 100), 57.0 (CH$_2$OCHCH$_2$$^+$, 73).

Synthesis of 2-[(2-methoxyethoxy)methyl]thiirane ("G$_1$S")

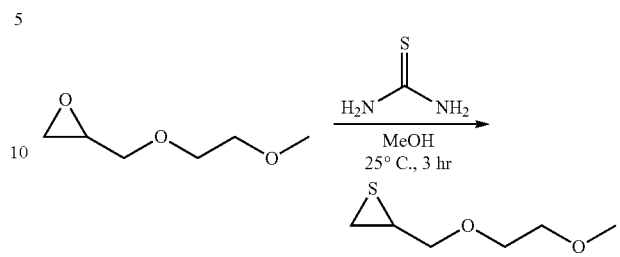

2-[(2-Methoxyethoxy)methyl]oxirane (5.2842 g, 40.0 mmol) was added to a 250 mL flask and dissolved in MeOH (100 mL). To this, thiourea (30.5247 g, 401.0 mmol) was added while stirring at ambient temperature and atmosphere. After 3 h the milky white dispersion was filtered through a medium glass frit, diluted with Et$_2$O (100 mL) and washed with H$_2$O (20 mL, ×6). The organic phase was dried via Na$_2$SO$_4$, passed through a short plug of silica, and solvent removed under reduced pressure. The pure product was received as a clear-colorless liquid in 71.0% yield (4.2067 g, 28.4 mmol) which was dried via CaH$_2$ under an argon atmosphere over 48 hours in a −10° C. freezer and then passed through a 0.2 μm filter and stored at −10° C. until use. $^1$H NMR (300 MHz, CDCl$_3$): δ/ppm 3.73-3.45 (m, 6H), 3.40 (s, 3H), 3.10 (m, 1H), 2.53 (dt, J=6.2, 1.1 Hz, 1H), 2.22 (dd, J=5.4, 1.3 Hz, 1H); $^{13}$C NMR (75 MHz, CDCl$_3$): δ/ppm 76.01, 71.90, 70.35, 59.14, 31.99, 23.94.

Synthesis of 1,2-bis(2,3-epithiopropoxy)ethane mixture ("SG$_x$S")

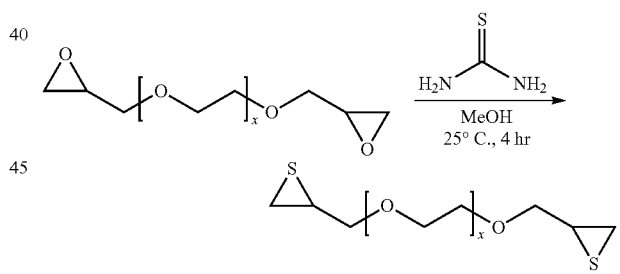

Ethylene glycol diglycidyl ether mixture (x=1-3, 3.4532 g, 19.846 mmol) was added to a 250 mL RBF and dissolved in MeOH (50 mL). To this thiourea (38.5424 g, 506.337 mmol) was added and the resulting white mixture was allowed to stir at ambient temperature and pressure for 4 hours. Following this the milky white dispersion was filtered through a medium glass frit, diluted with Et$_2$O (100 mL), and washed with H$_2$O (×10, 25 mL). The organic layer was dried via Na$_2$SO$_4$, passed through a plug of silica, and solvent removed under reduced pressure. The pure product was received as a viscous clear-colorless liquid in 29.6% yield (1.2113 g, 5.872 mmol) which was dried via CaH$_2$ under an argon atmosphere over 1 week in a −10° C. freezer and then passed through a 0.2 μm filter and stored at −10° C. until used. $^1$H NMR (300 MHz, CDCl$_3$): δ/ppm 3.79-3.49 (m, 8H), 3.14-3.06 (m, 1H), 2.55-2.51 (m, 1H), 2.25-2.20 (m, 1H); $^{13}$C NMR (75 MHz, CDCl$_3$): δ/ppm 78.76, 78.69, 75.96, 75.88, 75.26, 75.15, 70.98, 70.86, 70.78, 70.41, 70.37, 43.85, 32.28, 32.09, 32.05, 23.83, 23.74.

Discussion Commercially available episulfides such as ethylene sulfide (ES) and propylene sulfide (PS) can both be polymerized through the proposed AROP as reported by previous synthetic investigations.[30, 31] However, unlike the ether-based analog poly(ethylene oxide) (PEO), poly(ethylene sulfide) (PES) is a highly crystalline polymer through a wide temperature range, even in the presence of $Li^+$ salts. PES also displays very poor solubility in almost all solvents at ambient temperatures.[32, 33] As a result of the methyl R-group present in PS, the derived polymer poly(propylene sulfide) (PPS) does not show the same crystalline behavior exhibited in PES.[34] However, PPS was initially found to be not polar enough to illicit a single phase with $Li^+$ salts in electrolyte solution, and thus does not produce a sufficiently ionically conductive medium for battery applications. To ensure an amorphous and homogeneous system new oligo (ethylene glycol) functionalized episulfide monomers: $G_1S$ and $SG_xS$, were developed:

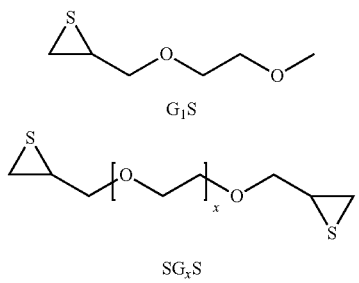

$G_1S$ $SG_xS$

During the polymerization, the 2-alkyloxyethoxy R-groups for both compounds assist in preventing the formation a crystal domain, increase the polarity of the derived polymers, and allow $Li^+$ coordination and conduction. The polymerization of the $G_1S$ monomer leads to a linear polymer similar to that of other episulfides, while the polymerization of the $SG_xS$ leads to a cross-linked polymer network due to its bis-episulfide functionality. The co-polymerization of $G_1S$ and $SG_xS$ is expected to result in an elastic polymer network with sufficient lithium-ion conductivity, ideal for polymer electrolyte applications.

Figure 1:
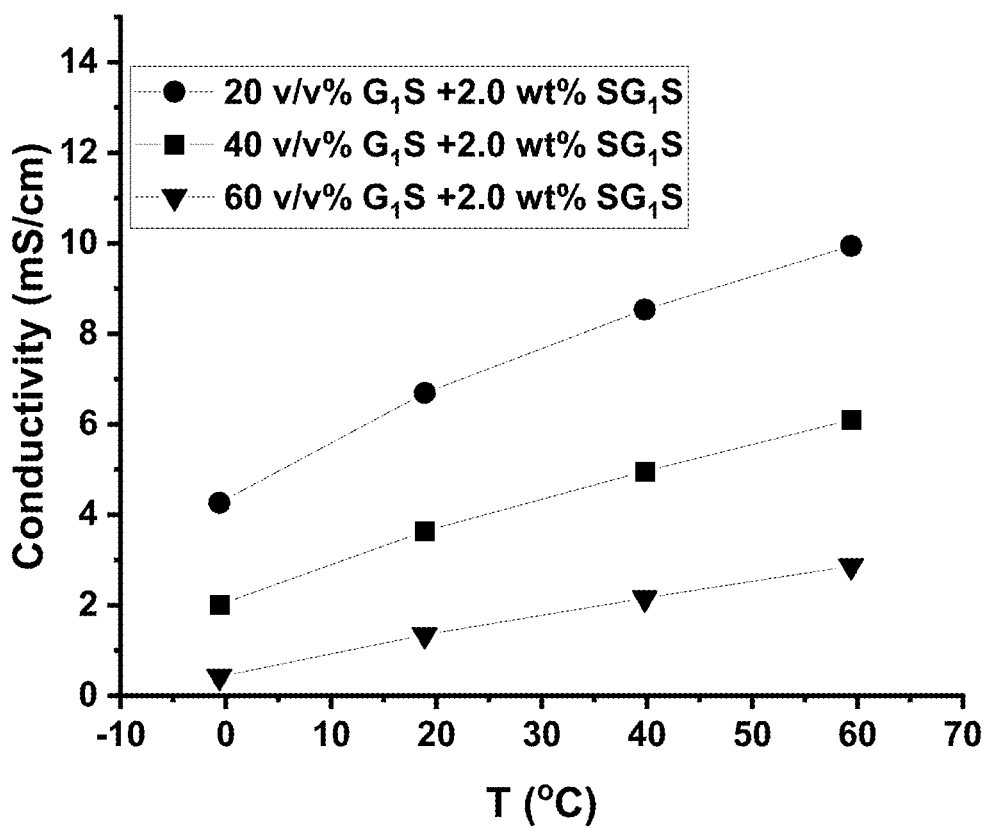
FIG. 1 is a graph of ionic conductivity of electrolyte formulations pre-(hollow) and post-polymerization (filled) vs temperature with 20%, 40% and 60% $G_1S$, where the remaining solvent volume is DOL:DME (1:1), all with 1.0 M LiTFSI and 2 wt % $SG_xS$ as cross-linker, according to the examples.

As expected, the addition of a nucleophilic base, such as $Li_2S_x$, readily initiates the polymerization of the new episulfide monomer solvents $G_1S$ and $SG_xS$. Electrolytes using $G_1S$ as a polymer precursor show no signs of lithium salt precipitation in the range of 20-60% v/v before or after polymerization initiated with $Li_2S_6$. The bulk ionic conductivity of the monomer and polymerized electrolytes was measured by electrochemical impedance spectroscopy (EIS). As expected, increased polymer content led to a decreased ionic conductivity of the electrolyte with values at ambient conditions (25° C.) found to be 6.9, 4.2, and 3.4 mS/cm for 20, 40, and 60% $G_1S$, respectively before polymerization, and 6.7, 3.6, and 1.3 mS/cm post-polymerization. FIG. 1. Increases in temperature produced an increase in ionic conductivity from 25° C. to 60° C. with value between 9.9-2.9 mS/cm for 20% and 60% $G_1S$, respectively.

Figure 2:
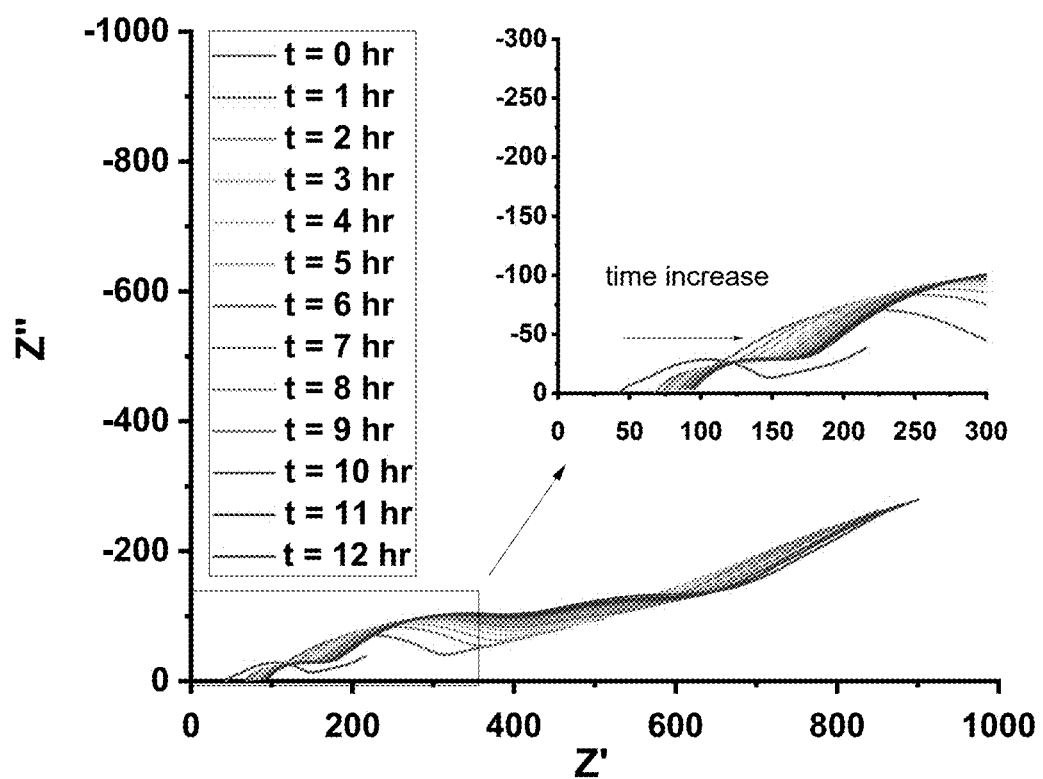
FIG. 2 is a graph of electrochemical impedance spectroscopy (EIS) spectra of freshly made Li—S cell with 1 M LiTFSI DOL:DME:$G_1S$ (30:30:40)+2 wt % $SG_xS$ as the electrolyte measured every hour over a 12 h rest at open circuit voltage (OCV), according to the examples.

To validate the in situ formation of polymer electrolyte in a Li—S cell, EIS was conducted using 2032 coin cell with the $G_1S$ and $SG_xS$ monomer every hour on a freshly assembled Li—S cell. Self-discharge of the sulfur-based cathode generates $Li_2S_x$ which simultaneously initiates AROP in the electrolyte. As shown in FIG. 2, the polymerization of $G_1S$ with 2 wt % $SG_xS$ as a crosslinker largely reaches a steady state within 2 hours as indicated by the shift of the interception of x-axis at the high frequency to high resistance values. This indicates that the bulk conductivity of the electrolyte has reached a constant and the polymerization is largely concluded with a negligible shift in the Z'>2 h.

Figure 3:
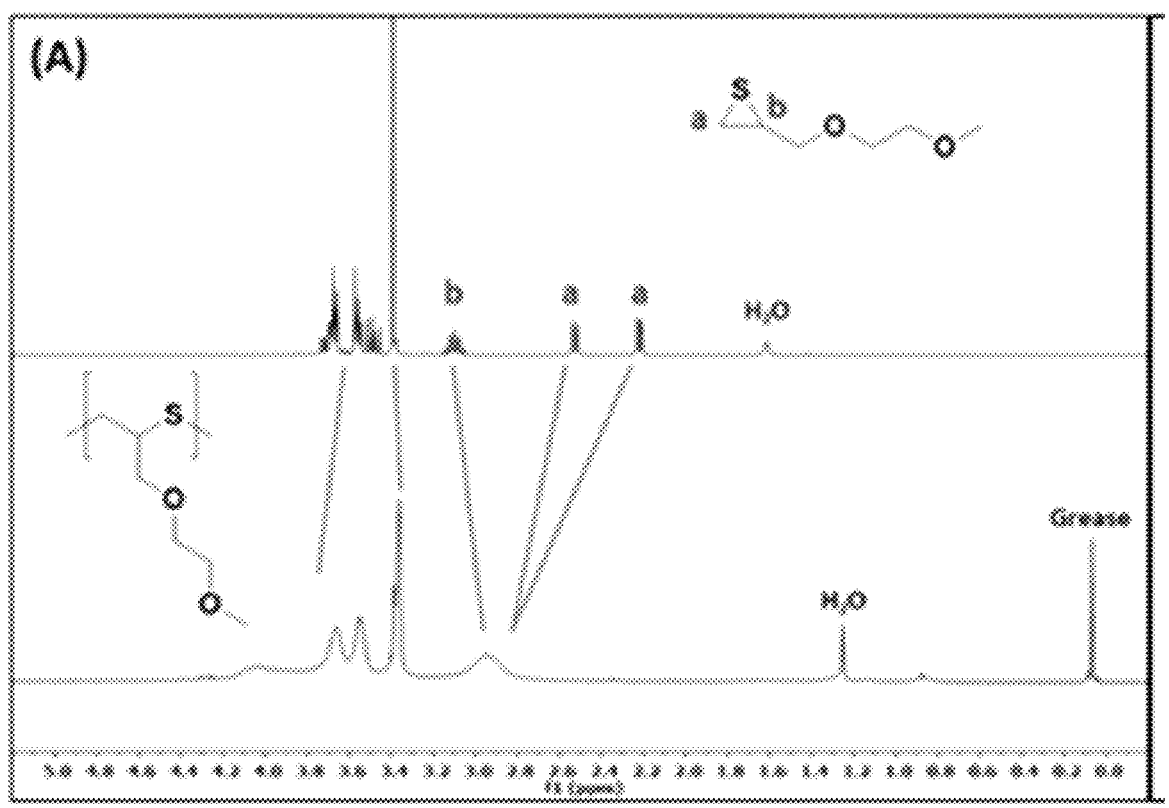
FIG. 3 is the $^1H$ NMR spectra of $PG_1S$ harvested from Li—S cells after formation cycles, according to the examples.

FIG. 3 is the before and after polymerization $^1H$ NMR spectra of $PG_1S$ based on the harvested polymer from Li—S cells after formation cycles. Labeled are the two sets of hydrogen atoms of the episulfide functionality with chemical shift values of 2.22 and 2.53 ppm for the methylene ($CH_2$) position and 3.10 ppm for the methine (CH) position for the monomer (labeled "a" and "b" respectively). After polymerization these peaks shift to a single broad peak at 2.94 ppm, which integrates to 3 hydrogens relative to the signal at 3.39 ppm which represents the methyl ($CH_3$) of the glyme R-group. This is consistent with the ex situ polymerization of episulfides and directly indicates the capability of $G_1S$ to polymerize in situ using the environment present in Li—S cells. Gel permeation chromatography (GPC) testing was also conducted in DMF and LiBr, and it confirms the presence of polymer in the prepared sample. The average $M_w$ was calculated to be 16 kDa with a polydispersity index (PDI) of 1.55 relative to polyethyleneoxide (PEO) standards.

A lithium/lithium symmetric cell was cycled at an equivalent current of 0.1 C (0.2 $mA/cm^2$). The polymer electrolytes formed from 20% and 40% $G_1S$ showed a minimal overpotential over 400 h of testing (200 cycles). In contrast, the electrolyte containing 60% $G_1S$ did show a moderate rise in overpotential with a stable value at around 0.25 V. Overall, even the over-potential observed for the highest polymer content show promising results over the test range of 400 h indicating the polymer electrolytes were able to form a stable SEI on the lithium anode. Furthermore, cyclic voltammetry (CV) of the un-polymerized electrolyte with 30% $G_1S$ showed no indication of oxidation up to 3.0 V. From 3.0 V to 5.0 V the cells exhibited an irreversible oxidation peak starting at about 3.36 V, and which can be attributed to the oxidation of the oligoether portion of the polymer electrolyte and ether based co-solvents.

Figure 4A:
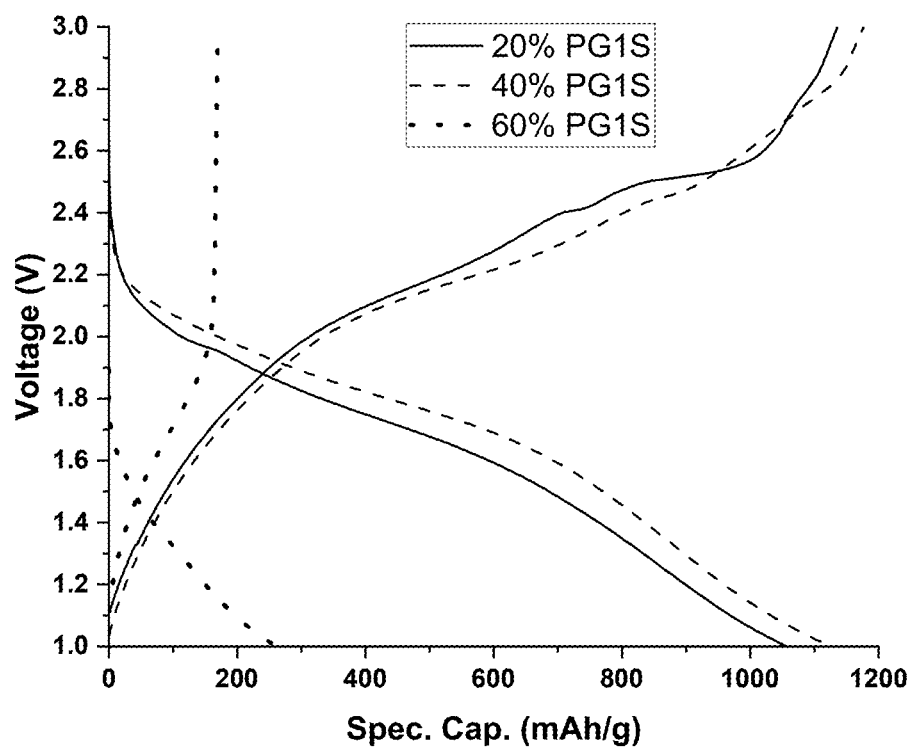
FIGS. 4A and B are graphs of the 1$^{st}$ charge-discharge voltage profiles (4A) and specific discharge capacity (4B) of Li—S cells with in situ generated polymer electrolyte where $G_1S$=20%, 40%, and 60% and the remaining volume is DOL:DME (1:1), all electrolytes are 2 wt % $SG_xS$ and 1.0 M LiTFSI at 0.1C, according to the examples.
Figure 4B:
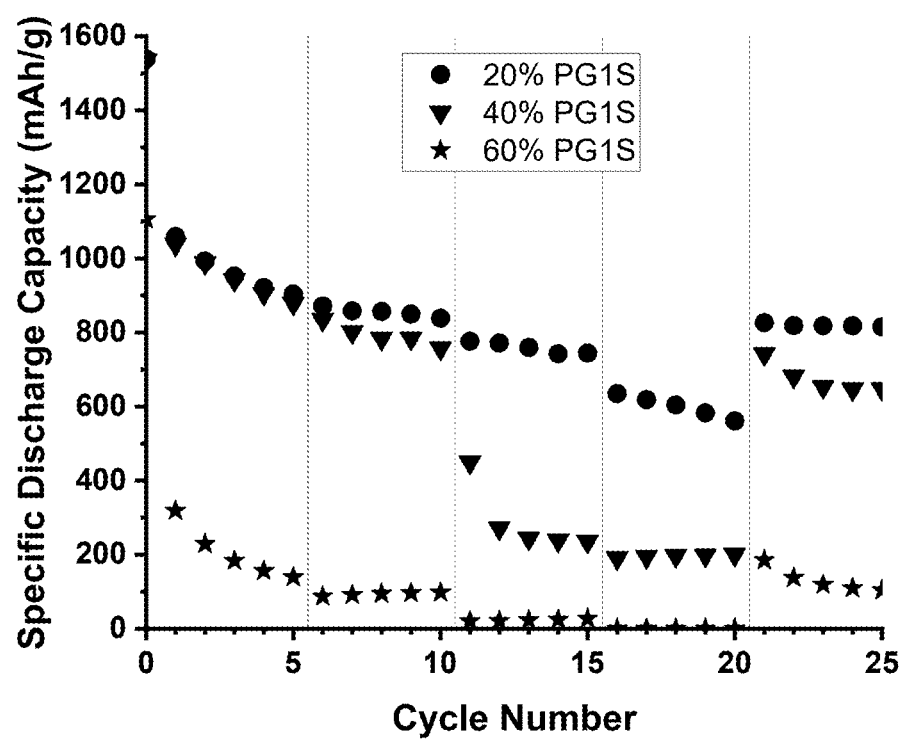

Li—S cell cycling performance of the in situ generated polymer electrolyte provided promising results for cells with sulfurized polyacrylonitrile (SPAN) as the cathode and lithium metal as anode. It should be noted that SPAN typically does not exhibit soluble polysulfides except in extended cycling in ether electrolytes; however, the surface-based lithium sulfide moieties[36-38] are equally as capable of initiating AROP based off harvested in situ polymer NMR spectroscopy. FIGS. 4A and 4B shows the charge-discharge voltage profiles for the first cycle with varied $G_1S$ amount at ambient temperature. Electrolytes with higher polymer content (60% v/v) shows lower capacity of 261 mAh/g, which is believed to be due to high polarization, a result of a lower conductivity of the electrolyte. Both the intermediary and lower polymer containing electrolyte (20 and 40% v/v) exhibited good specific capacity in the first cycle with values of 1056 and 1125 mAh/g at C/10. It should be noted that the initial discharge of the Li—S cell is considered as "cycle 0," the $1^{st}$ cycle discharge is that which takes place after the $1^{st}$ charge step and is an important distinction to be made when calculating the Coulombic efficiency for Li—S batteries.

Figure 5:
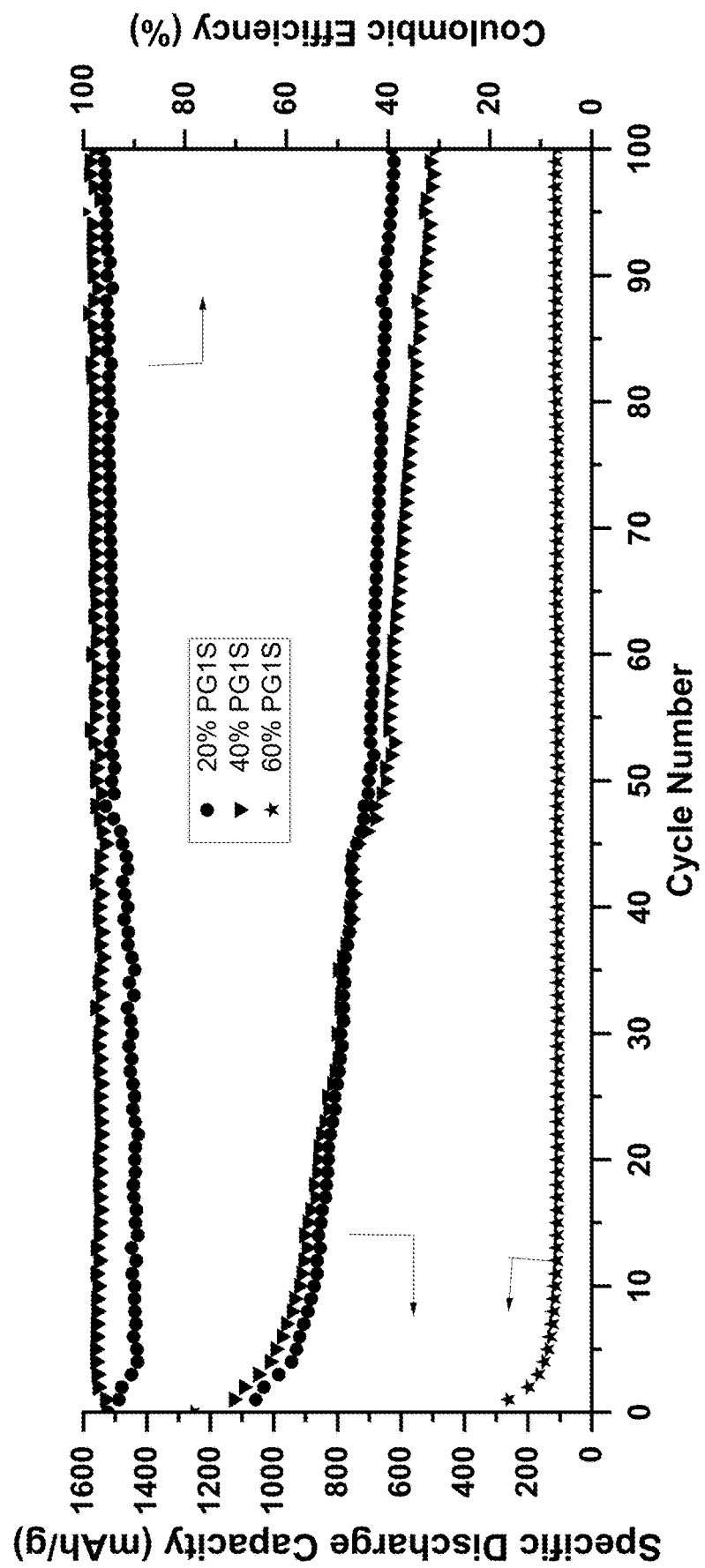
FIG. 5 is a dual graph of cell capacity and Coulombic efficiency versus cycle number, according to the examples.

The cell performance of the three formulations in Li—S cells is shown in FIG. 5 with the specific discharge capacity and Coulombic efficiency. The higher polymer content electrolyte (60% v/v) exhibited a dramatic decrease in the discharge capacity after the initial discharge eventually leveling out at 112 mAh/g after the first 10 cycles. The intermediary and lower polymer containing electrolytes (40% and 20% v/v) displayed improved specific discharge capacity retention with values of 505 and 651 mAh/g respectively after 100 cycles. In addition, the presence of the polymer electrolyte was found to lead to a significant improvement in Coulombic efficiency with average values of 92±2% and 97.5±0.7% for 20% and 40% v/v $G_1S$ respectively over 100 cycles without the use of lithium anode passivating additives (such as $LiNO_3$) which are normally used in ether based electrolytes to block polysulfide shuttling and increase Coulombic efficiency.

To understand the performance of these electrolyte systems in response to varied currents C-rate tests were conducted in Li—S cells assembled with the three polymer electrolytes studied. Due to the lower ionic conductivity of 60% v/v $G_1S$ (star symbol) the C-rate performance was fairly poor with almost no capacity observed at 0.5C and 1.0C. In contrast, 40% and 20% $G_1S$ showed much better performance with only a modest decrease in discharge capacity observed for 0.2C for both electrolytes. Surprisingly the electrolyte composed of 40% $G_1S$ still showed >200 mAh/g specific discharge capacity even at currents as high as 0.5C and 1.0C. However, the rate test did show that the slightly lower conductivity of the 40% $G_1S$ formulation becomes an issue at increased cycling rates while the 20% formulation had little issue.

Figures 6A, 6B, 6C, 6D, 6E, 6F:
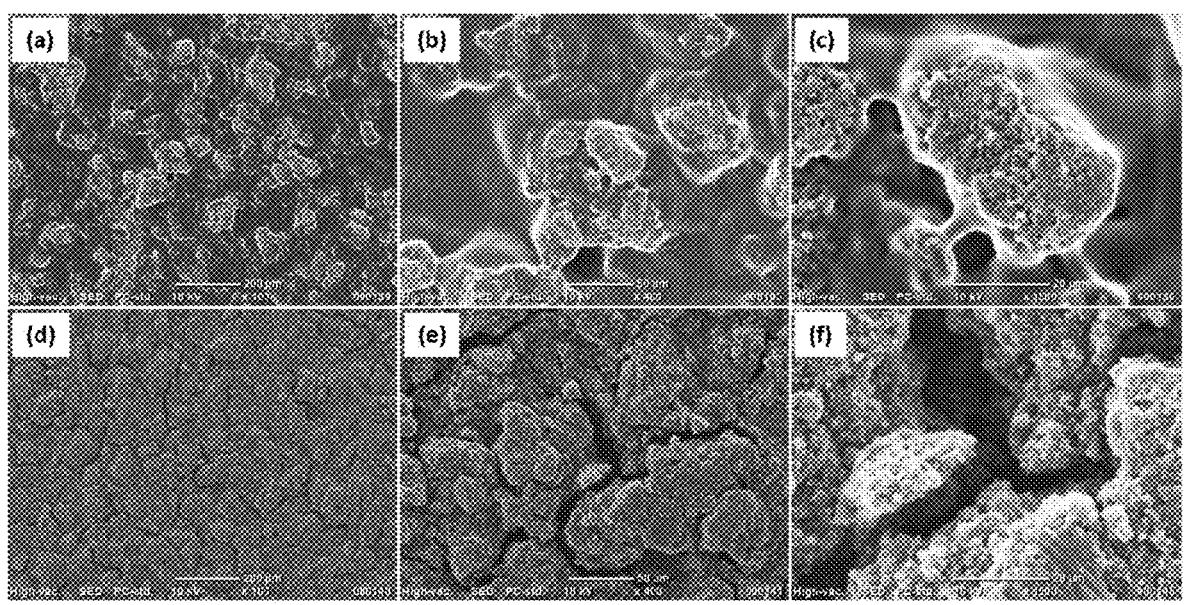
FIGS. 6A-6F are SEM images of cycled SPAN cathodes at different magnification with in situ polymer electrolyte.

FIGS. 6A, 6B, and 6C are SEM images of SPAN cathodes cycled in electrolyte of DOL:DME:$G_1S$ (30:30:40)+2 wt % $SG_xS$; and FIGS. 6D, 6E, and 6F are images of the cycled electrode with a state of the art liquid electrolyte 1 M LiTFSI DOL:DME (50:50) electrolyte for reference. It is immediately observed that the electrode cycled in the presence of the new polymerizable electrolyte solvent has formed a coating of organic polymer over the entire electrode surface and within the pores and cracks while the reference blatantly lacks this feature. As to be expected, the polymer electrolyte was found in all parts of the coin cell as the polymerization can propagate out from the cathode throughout the cell. Polymer was found inside the separator. The presence of polymer on the lithium anode surface was not observed by SEM due to the lack of porosity in the metal surface and the fact that any residual polymer was washed away during SEM sample preparation.

In summary, it has now been demonstrated for the first time an authentic fully in situ formed polymer electrolyte using liquid precursors and a Lewis base that initiates anion ring-opening polymerization in the Li—S cell. It was shown that new electrolyte precursors, $G_1S$ and $SG_xS$, having episulfide functionality, are capable of polymerizing in situ immediately after the assembly of Li—S cells without the addition of any external initiator. The designed AROP system utilizes the inherent chemistry of the Li—S battery, namely the self-generated nucleophilic lithium polysulfide species, as a Lewis base initiator. The polymerization was able to be completed within 2 hours and produced polymer electrolytes with bulk ionic conductivities in the range of 6.9-3.4 mS/cm for 20-60% $G_1S$ in the presence of DOL:DME 1.0 M LiTFSI+2 wt % $SG_xS$. The formation of the polymer electrolyte was monitored and confirmed by NMR, GPC, and SEM. The polymer electrolyte showed promising Li—S battery performance with specific discharge capacities of 505 mAh/g for electrolytes containing 40% $G_1S$ and 97.5% Coulombic efficiencies over 100 cycles. This work offers an important pathway toward polymer electrolytes for high performance Li—S batteries with improved safety and efficiencies.

Non-sulfur-based system. A $LiFeO_4$/Li cell was prepared that includes a gel polymer electrolyte having 70 wt % dioxolane, 25 wt % $G_1S$, 5 wt % $SG_1S$, 1.0 M LiTFSI, and 0.1 M initiator. The cycling voltage v. specific capacity is presented in FIG. 7.

REFERENCES

1. J. Scheers, S. Fantini and P. Johansson, *J. Power Sources,* 2014, 255, 204-218.
2. X. Ji, K. T. Lee and L. F. Nazar, *Nature Materials,* 2009, 8, 500-506.
3. H.-J. Peng, J.-Q. Huang, X.-B. Cheng and Q. Zhang, *Adv. Energy Mater.,* 2017, 7, 1700260.
4. J. R. Nair, L. Imholt, G. Brunklaus and M. Winter, *The Electrochemical Society Interface,* 2019, 28, 55-61.
5. X. Huang, B. Luo, R. Knibbe, H. Hu, M. Lyu, M. Xiao, D. Sun, S. Wang and L. Wang, *Chem.—Eur. J.,* 2018, 24, 18544.
6. Q. Li, H. Y. Sun, Y. Takeda, N. Imanishi, J. Yang and O. Yamamoto, *J. Power Sources,* 2001, 94, 201-205.
7. I. Ismail, A. Noda, A. Nishimoto and M. Watanabe, *Electrochim. Acta,* 2001, 46, 1595-1603.
8. H. Duan, Y.-X. Yin, X.-X. Zeng, J.-Y. Li, J.-L. Shi, Y. Shi, R. Wen, Y.-G. Guo and L.-J. Wan, *Energy Storage Materials,* 2018, 10, 85-91.
9. Y.-G. Cho, C. Hwang, D. S. Cheong, Y.-S. Kim and H.-K. Song, *Adv. Mat.,* 2019, 31, 1804909.
10. S. Z. Zhang, X. H. Xia, D. Xie, R. C. Xu, Y. J. Xu, Y. Xia, J. B. Wu, Z. J. Yao, X. L. Wang and J. P. Tu, *J. Power Sources,* 2019, 409, 31-37.
11. Z. Li, H.-X. Xie, X.-Y. Zhang and X. Guo, *J. Mater. Chem. A,* 2020, 8, 3892-3900.
12. G. L. Shebert, S. Zamani, C. Yi and Y. L. Joo, *J. Mater. Chem. A,* 2020, 8, 4341-4353.
13. Z. Yang, Y. Luo, X. Gao and R. Wang, *ChemElectroChem,* 2020, 7, 2599-2607.
14. W. J. Chung, J. J. Griebel, E. T. Kim, H. Yoon, A. G. Simmonds, H. J. Ji, P. T. Dirlam, R. S. Glass, J. J. Wie, N. A. Nguyen, B. W. Guralnick, J. Park, Á. Somogyi, P. Theato, M. E. Mackay, Y.-E. Sung, K. Char and J. Pyun, *Nature Chemistry,* 2013, 5, 518-524.
15. P. T. Dirlam, A. G. Simmonds, R. C. Shallcross, K. J. Arrington, W. J. Chung, J. J. Griebel, L. J. Hill, R. S. Glass, K. Char and J. Pyun, *ACS Macro Letters,* 2015, 4, 111-114.
16. A. G. Simmonds, J. J. Griebel, J. Park, K. R. Kim, W. J. Chung, V. P. Oleshko, J. Kim, E. T. Kim, R. S. Glass, C. L. Soles, Y.-E. Sung, K. Char and J. Pyun, *ACS Macro Letters,* 2014, 3, 229-232.
17. M. Alamgir, R. D. Moulton and K. M. Abraham, *Electrochim. Acta,* 1991, 36, 773-782.
18. F.-Q. Liu, W.-P. Wang, Y.-X. Yin, S.-F. Zhang, J.-L. Shi, L. Wang, X.-D. Zhang, Y. Zheng, J.-J. Zhou, L. Li and Y.-G. Guo, *Science Advances,* 2018, 4, eaat5383.
19. K. Khan, Z. Tu, Q. Zhao, C. Zhao and L. A. Archer, *Chem. Mater.,* 2019, 31, 8466-8472.
20. Q. Zhao, X. Liu, S. Stalin, K. Khan and L. A. Archer, *Nature Energy,* 2019, 4, 365-373.
21. F. Liu, T. Li, Y. Yang, J. Yan, N. Li, J. Xue, H. Huo, J. Zhou and L. Li, *Macromolecular Rapid Communications,* 2020, 41, 2000047.
22. Q. Liu, B. Cai, S. Li, Q. Yu, F. Lv, F. Kang, Q. Wang and B. Li, *J. Mater. Chem. A,* 2020, 8, 7197-7204.
23. P. Yang, X. Gao, X. Tian, C. Shu, Y. Yi, P. Liu, T. Wang, L. Qu, B. Tian, M. Li, W. Tang, B. Yang and J. B. Goodenough, *ACS Energy Lett.,* 2020, 5, 1681-1688.

24. C.-Z. Zhao, Q. Zhao, X. Liu, J. Zheng, S. Stalin, Q. Zhang and L. A. Archer, *Adv. Mat.*, 2020, 32, 1905629.
25. P. Dubois, O. Coulembier and J.-M. Raquez, *Handbook of ring-opening polymerization*, John Wiley & Sons, 2009.
26. O. Nuyken and S. D. Pask, *Polymers*, 2013, 5, 361-403.
27. T. Yim, M.-S. Park, J.-S. Yu, K. J. Kim, K. Y. Im, J.-H. Kim, G. Jeong, Y. N. Jo, S.-G. Woo and K. S. Kang, *Electrochim. Acta*, 2013, 107, 454-460.
28. Q. Pang, X. Liang, C. Y. Kwok and L. F. Nazar, *Nature Energy*, 2016, 1, 1-11.
29. P. B. Balbuena and Y. Wang, *Lithium-ion batteries: solid-electrolyte interphase*, Imperial college press, 2004.
30. A. Duda and S. Penczek, *Macromolecules*, 1982, 15, 36-40.
31. C. E. Brubaker, D. Velluto, D. Demurtas, E. A. Phelps and J. A. Hubbell, *Acs Nano*, 2015, 9, 6872-6881.
32. Y. Takahashi, H. Tadokoro and Y. Chatani, *Journal of Macromolecular Science, Part B: Physics*, 1968, 2, 361-367.
33. Y. Sasanuma and A. Watanabe, *Macromolecules*, 2006, 39, 1646-1656.
34. Y. Sasanuma, Y. Hayashi, H. Matoba, I. Touma, H. Ohta, M. Sawanobori and A. Kaito, *Macromolecules*, 2002, 35, 8216-8226.
35. C. Li, Q. Lan, Y. Yang, H. Shao and H. Zhan, *ACS Appl. Mater. Interfaces*, 2019, 11, 2479-2489.
36. W. Wang, Z. Cao, G. A. Elia, Y. Wu, W. Wahyudi, E. Abou-Hamad, A.-H. Emwas, L. Cavallo, L.-J. Li and J. Ming, *ACS Energy Lett.*, 2018, 3, 2899-2907.
37. M. Li, J. E. Frerichs, M. Kolek, W. Sun, D. Zhou, C. J. Huang, B. J. Hwang, M. R. Hansen, M. Winter and P. Bieker, *Adv. Funct. Mater.*, 2020, 30, 1910123.
38. J. Fanous, M. Wegner, J. Grimminger, Ä. Andresen and M. R. Buchmeiser, *Chem. Mater.*, 2011, 23, 5024-5028.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A battery comprising a cathode comprising a cathode active material, an anode comprising lithium, and an electrolyte comprising an aprotic solvent, a lithium salt, and a compound containing at least one epi-sulfide group;
wherein:
the compound is represented as [epi-sulfide]-[L]-[epi-sulfide], wherein L is a linker; or
the compound is represented as by Formula I:

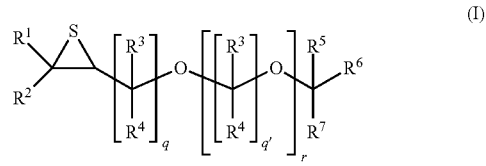

wherein:
each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl;
q is 0, 1, 2, or 3;
q' is 1, 2, 3, or 4; and
r is at least 1.

2. The battery of claim 1, wherein the electrolyte comprises a mixture of two or more different compounds each containing at least one epi-sulfide group.

3. The battery of claim 1, wherein each L is alkyl, ether, polyether, aryl, heteroaryl, or heterocyclyl.

4. The battery of claim 1, wherein the compound is represented by Formula I:

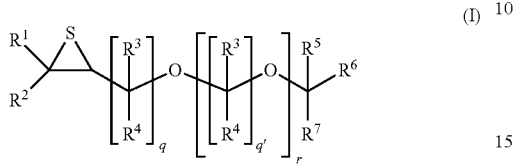

wherein:
- each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl;
- q is 0, 1, 2, or 3;
- q' is 1, 2, 3, or 4; and
- r is at least 1.

5. The battery of claim 1, wherein $R^1$, $R^2$, $R^3$, $R^4$, $R^5$, and $R^7$ are H or alkyl, $R^6$ is H, alkyl or

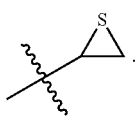

q is 1 or 2, q' is 1 or 2, and r is 0, 1, or 2.

6. The battery of claim 4, wherein the electrolyte comprises a mixture of two or more different compounds of Formula I.

7. The battery of claim 6, wherein the two or more different compounds of Formula I, represented as Formulae IA and IB:

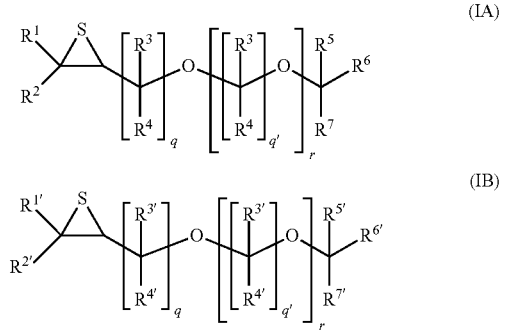

wherein:
- each $R^1$, $R^2$, $R^3$, $R^4$, $R^5$, $R^6$, and $R^7$ is individually H, alkyl, alkoxy, aryl, aralkyl, heteroaryl, heteroaralkyl, heterocyclylalkoxyl, heterocyclyl, or heterocyclylalkyl;
- each $R^{1'}$, $R^{2'}$, $R^{3'}$, $R^{4'}$, $R^{5'}$, $R^{6'}$, and $R^{7'}$ is individually H, alkyl, alkoxy, aryl, aralkyl, heteroaryl, heteroaralkyl, heterocyclylalkoxyl, heterocyclyl, or heterocyclylalkyl, with the proviso that at least one $R^{1'}$, $R^{2'}$, $R^{3'}$, $R^{4'}$, $R^{5'}$, $R^{6'}$, and $R^{7'}$ contains a heterocyclyl group;
- each q is individually 0, 1, 2, or 3;
- each q' is individually 1, 2, 3, or 4; and
- each r individually is at least 1.

8. The battery of claim 7, wherein each $R^1$, $R^2$, $R^3$, $R^4$, $R^5$, $R^6$, and $R^7$ are individually H or alkyl; each q is individually 1 or 2; each q' is individually 1 or 2; each r is individually 0, 1, or 2; and each $R^{1'}$, $R^{2'}$, $R^{3'}$, $R^{4'}$, $R^{5'}$, and $R^{6'}$ individually is H or alkyl, and $R^{7'}$ is heterocyclyl.

9. The battery of claim 7, wherein each $R^1$, $R^2$, $R^3$, $R^4$, $R^5$, $R^6$, and $R^7$ are individually H or alkyl; each q is individually 1 or 2; each q' is individually 1 or 2; each r is individually 0, 1, or 2; and each $R^{1'}$, $R^{2'}$, $R^{3'}$, $R^{4'}$, $R^{5'}$, and $R^{6'}$ individually is H or alkyl, and $R^{7'}$ is

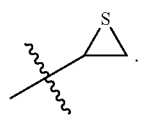

10. The battery of claim 7, wherein $R^1$, $R^2$, $R^3$, $R^4$, $R^5$, $R^6$, and $R^7$ are H; each q is individually 1 or 2; each q' is individually 1 or 2; and each r is individually 0, 1, or 2; $R^{1'}$, $R^{2'}$, $R^{3'}$, $R^{4'}$, $R^{5'}$, and $R^{6'}$ are H, and $R^{7'}$ is

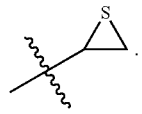 [SMILES: *C1CS1]

11. The battery of claim 1, wherein the compound is a mixture of $G_1S$ and $SG_xS$:

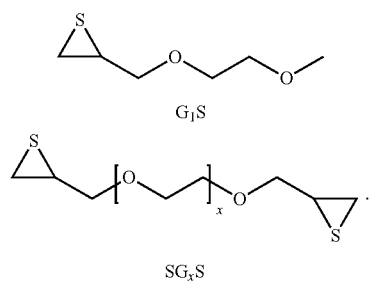

12. The battery of claim 1, wherein the cathode active material comprises sulfur.

* * * * *